(12) United States Patent
Garrison et al.

(10) Patent No.: US 10,743,893 B2
(45) Date of Patent: Aug. 18, 2020

(54) METHODS AND SYSTEMS FOR TREATMENT OF ACUTE ISCHEMIC STROKE

(71) Applicant: Route 92 Medical, Inc., San Mateo, CA (US)

(72) Inventors: Michi E. Garrison, San Mateo, CA (US); Tony M. Chou, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 0 days.

(21) Appl. No.: 16/796,139

(22) Filed: Feb. 20, 2020

(65) Prior Publication Data
US 2020/0187965 A1 Jun. 18, 2020

Related U.S. Application Data

(63) Continuation of application No. 16/117,753, filed on Aug. 30, 2018, now Pat. No. 10,646,239, which is a
(Continued)

(51) Int. Cl.
*A61B 17/22* (2006.01)
*A61M 25/06* (2006.01)
(Continued)

(52) U.S. Cl.
CPC ............ *A61B 17/22* (2013.01); *A61B 17/221* (2013.01); *A61M 1/0072* (2014.02);
(Continued)

(58) Field of Classification Search
CPC .................. A61B 17/22; A61B 17/221; A61B 2017/22094
(Continued)

(56) References Cited

U.S. PATENT DOCUMENTS 2,623,520 A 12/1952 Bamford, Jr. et al.
3,612,050 A 10/1971 Sheridan
(Continued)

FOREIGN PATENT DOCUMENTS

CN 103260689 A 8/2013
DE 102006039236 A1 2/2008
(Continued)

OTHER PUBLICATIONS

U.S. Appl. No. 13/921,165, filed Jun. 18, 2013, US 2013-0281788.
(Continued)

*Primary Examiner* — Andrew J Mensh
(74) *Attorney, Agent, or Firm* — Mintz Levin Cohn Ferris Glovsky and Popeo, P.C.

(57) ABSTRACT

Described are methods and systems for transcervical access of the cerebral arterial vasculature and treatment of cerebral occlusions, including ischemic stroke. The methods and devices may include methods and devices which may provide aspiration and passive flow reversal, those which protect the cerebral penumbra during the procedure to minimize injury to brain, as well as distal catheters and devices to remove an occlusion. The methods and devices that provide passive flow reversal may also offer to the user a degree of flow control. Devices and methods which provide a way to securely close the access site in the carotid artery to avoid the potentially devastating consequences of a transcervical hematoma are also described.

12 Claims, 22 Drawing Sheets

Related U.S. Application Data continuation of application No. 13/566,451, filed on Aug. 3, 2012, now Pat. No. 10,327,790.

(60) Provisional application No. 61/579,581, filed on Dec. 22, 2011, provisional application No. 61/547,597, filed on Oct. 14, 2011, provisional application No. 61/543,019, filed on Oct. 4, 2011, provisional application No. 61/515,736, filed on Aug. 5, 2011.

(51) Int. Cl.

| | | |
|---|---|---|
| *A61M 1/00* | (2006.01) | |
| *A61B 17/221* | (2006.01) | |
| *A61M 1/10* | (2006.01) | |
| *A61M 1/36* | (2006.01) | |
| *A61M 25/00* | (2006.01) | |
| *A61M 25/01* | (2006.01) | |
| *A61F 2/01* | (2006.01) | |
| *A61B 17/3203* | (2006.01) | |

(52) U.S. Cl.
CPC ........ *A61M 1/1037* (2013.01); *A61M 1/3621* (2013.01); *A61M 25/0662* (2013.01); *A61B 17/32037* (2013.01); *A61B 2017/2212* (2013.01); *A61B 2017/2217* (2013.01); *A61B 2017/22034* (2013.01); *A61B 2017/22038* (2013.01); *A61B 2017/22039* (2013.01); *A61B 2017/22044* (2013.01); *A61B 2017/22054* (2013.01); *A61B 2017/22084* (2013.01); *A61B 2017/22094* (2013.01); *A61F 2/013* (2013.01); *A61M 1/1062* (2014.02); *A61M 25/0068* (2013.01); *A61M 25/0169* (2013.01); *A61M 2025/0681* (2013.01)

(58) Field of Classification Search
USPC ........................ 604/8, 9, 508, 509, 523, 159
See application file for complete search history.

(56) References Cited

U.S. PATENT DOCUMENTS

| | | |
|---|---|---|
| 3,631,848 A | 1/1972 | Muller |
| 4,013,080 A | 3/1977 | Froning |
| 4,571,240 A | 2/1986 | Samson et al. |
| 4,771,777 A | 9/1988 | Horzewski et al. |
| 4,840,690 A | 6/1989 | Melinyshyn et al. |
| 4,865,581 A | 9/1989 | Lundquist et al. |
| 4,921,478 A | 5/1990 | Solano et al. |
| 4,921,479 A | 5/1990 | Grayzel |
| 4,946,440 A | 8/1990 | Hall |
| 4,946,443 A | 8/1990 | Hauser et al. |
| 4,994,033 A | 2/1991 | Shockey et al. |
| 5,135,484 A | 8/1992 | Wright |
| 5,250,060 A | 10/1993 | Carbo et al. |
| 5,257,979 A | 11/1993 | Jagpal |
| 5,269,297 A | 12/1993 | Weng et al. |
| 5,303,714 A | 4/1994 | Abele et al. |
| 5,312,356 A | 5/1994 | Engelson et al. |
| RE34,633 E | 6/1994 | Sos et al. |
| 5,318,032 A | 6/1994 | Lonsbury et al. |
| 5,324,262 A | 6/1994 | Fischell et al. |
| 5,328,471 A | 7/1994 | Slepian |
| 5,338,300 A | 8/1994 | Cox |
| 5,370,623 A | 12/1994 | Kreamer |
| 5,380,284 A | 1/1995 | Don Michael |
| 5,385,562 A | 1/1995 | Adams et al. |
| 5,429,605 A | 7/1995 | Richling et al. |
| 5,437,632 A | 8/1995 | Engelson |
| 5,443,454 A | 8/1995 | Tanabe et al. |
| 5,454,795 A | 10/1995 | Samson |
| 5,476,450 A | 12/1995 | Ruggio |
| 5,484,407 A | 1/1996 | Osypka |
| 5,484,412 A | 1/1996 | Pierpont |
| 5,484,418 A | 1/1996 | Quiachon et al. |
| 5,492,530 A | 2/1996 | Fischell et al. |
| 5,496,294 A | 3/1996 | Hergenrother et al. |
| 5,522,836 A | 6/1996 | Palermo |
| 5,527,292 A | 6/1996 | Adams et al. |
| 5,542,937 A | 8/1996 | Chee et al. |
| 5,549,601 A | 8/1996 | McIntyre et al. |
| 5,558,635 A | 9/1996 | Cannon |
| 5,573,520 A | 11/1996 | Schwartz et al. |
| 5,599,326 A | 2/1997 | Carter |
| 5,628,754 A | 5/1997 | Shevlin et al. |
| 5,658,264 A | 8/1997 | Samson |
| 5,658,309 A | 8/1997 | Berthiaume et al. |
| 5,667,499 A | 9/1997 | Welch et al. |
| 5,693,029 A | 12/1997 | Leonhardt |
| 5,695,483 A | 12/1997 | Samson |
| 5,702,373 A | 12/1997 | Samson |
| 5,707,376 A | 1/1998 | Kavteladze et al. |
| 5,730,734 A | 3/1998 | Adams et al. |
| 5,749,849 A | 5/1998 | Engelson |
| 5,749,858 A | 5/1998 | Cramer |
| 5,776,141 A | 7/1998 | Klein et al. |
| 5,794,629 A | 8/1998 | Frazee |
| 5,795,341 A | 8/1998 | Samson |
| 5,810,869 A | 9/1998 | Kaplan et al. |
| 5,827,229 A | 10/1998 | Auth et al. |
| 5,833,650 A | 11/1998 | Imran |
| 5,836,926 A | 11/1998 | Peterson et al. |
| 5,836,955 A | 11/1998 | Buelna et al. |
| 5,843,051 A | 12/1998 | Adams et al. |
| 5,846,251 A | 12/1998 | Hart |
| 5,851,210 A | 12/1998 | Torossian |
| 5,853,400 A | 12/1998 | Samson |
| 5,876,367 A | 3/1999 | Kaganov et al. |
| 5,876,375 A | 3/1999 | Penny |
| 5,876,386 A | 3/1999 | Samson |
| 5,882,334 A | 3/1999 | Sepetka et al. |
| 5,895,399 A | 4/1999 | Barbut et al. |
| 5,908,407 A | 6/1999 | Frazee et al. |
| 5,913,848 A | 6/1999 | Luther et al. |
| 5,916,208 A | 6/1999 | Luther et al. |
| 5,921,952 A | 7/1999 | Desmond, III et al. |
| 5,928,192 A | 7/1999 | Maahs |
| 5,935,122 A | 8/1999 | Fourkas et al. |
| 5,938,645 A | 8/1999 | Gordon |
| 5,957,882 A | 9/1999 | Nita et al. |
| 5,976,093 A | 11/1999 | Jang |
| 5,976,178 A | 11/1999 | Goldsteen et al. |
| 5,997,508 A | 12/1999 | Lunn et al. |
| 5,997,523 A | 12/1999 | Jang |
| 6,004,310 A | 12/1999 | Bardsley et al. |
| 6,013,085 A | 1/2000 | Howard |
| 6,022,336 A | 2/2000 | Zadno-Azizi et al. |
| 6,022,340 A | 2/2000 | Sepetka et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,110,139 A | 8/2000 | Loubser |
| 6,120,480 A | 9/2000 | Zhang et al. |
| 6,139,524 A | 10/2000 | Killion |
| 6,142,958 A | 11/2000 | Hammarstrom et al. |
| 6,146,370 A | 11/2000 | Barbut |
| 6,146,373 A | 11/2000 | Cragg et al. |
| 6,146,415 A | 11/2000 | Fitz |
| 6,152,909 A | 11/2000 | Bagaoisan et al. |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,197,016 B1 | 3/2001 | Fourkas et al. |
| 6,206,868 B1 | 3/2001 | Parodi |

(56) References Cited

U.S. PATENT DOCUMENTS

| | | |
|---|---|---|
| 6,210,370 B1 | 4/2001 | Chi-Sing et al. |
| 6,228,052 B1 | 5/2001 | Pohndorf |
| 6,234,971 B1 | 5/2001 | Jang |
| 6,238,430 B1 | 5/2001 | Klumb et al. |
| 6,254,628 B1 | 7/2001 | Wallace et al. |
| 6,258,080 B1 | 7/2001 | Samson |
| 6,270,477 B1 | 8/2001 | Bagaoisan et al. |
| 6,277,115 B1 | 8/2001 | Saadat |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,309,379 B1 | 10/2001 | Willard et al. |
| 6,364,900 B1 | 4/2002 | Heuser |
| 6,368,316 B1 | 4/2002 | Jansen et al. |
| 6,368,344 B1 | 4/2002 | Fitz |
| 6,379,325 B1 | 4/2002 | Benett et al. |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,454,741 B1 | 9/2002 | Muni et al. |
| 6,458,151 B1 | 10/2002 | Saltiel |
| 6,464,664 B1 | 10/2002 | Jonkman et al. |
| 6,475,195 B1 | 11/2002 | Voda |
| 6,475,244 B2 | 11/2002 | Herweck et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,508,824 B1 | 1/2003 | Flaherty et al. |
| 6,517,520 B2 | 2/2003 | Chang et al. |
| 6,527,746 B1 | 3/2003 | Oslund et al. |
| 6,533,800 B1 | 3/2003 | Barbut |
| 6,540,712 B1 | 4/2003 | Parodi et al. |
| 6,544,276 B1 | 4/2003 | Azizi |
| 6,549,800 B1 | 4/2003 | Atalar et al. |
| 6,551,268 B1 | 4/2003 | Kaganov et al. |
| 6,551,302 B1 | 4/2003 | Rosinko et al. |
| 6,555,057 B1 | 4/2003 | Barbut et al. |
| 6,562,049 B1 | 5/2003 | Norlander et al. |
| 6,562,052 B2 | 5/2003 | Nobles et al. |
| 6,579,260 B2 | 6/2003 | Maki et al. |
| 6,582,390 B1 | 6/2003 | Sanderson |
| 6,582,396 B1 | 6/2003 | Parodi |
| 6,582,448 B1 | 6/2003 | Boyle et al. |
| 6,595,953 B1 | 7/2003 | Coppi et al. |
| 6,595,980 B1 | 7/2003 | Barbut |
| 6,605,074 B2 | 8/2003 | Zadno-Azizi et al. |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,673,025 B1 | 1/2004 | Richardson et al. |
| 6,676,637 B1 | 1/2004 | Bonnette et al. |
| 6,679,893 B1 | 1/2004 | Tran |
| 6,682,505 B2 | 1/2004 | Bates et al. |
| 6,685,672 B1 | 2/2004 | Forman |
| 6,685,722 B1 | 2/2004 | Rosenbluth et al. |
| 6,692,473 B2 | 2/2004 | St. Cyr et al. |
| 6,702,782 B2 | 3/2004 | Miller et al. |
| 6,706,055 B2 | 3/2004 | Douk et al. |
| 6,711,436 B1 | 3/2004 | Duhaylongsod |
| 6,716,183 B2 | 4/2004 | Clayman et al. |
| 6,719,717 B1 | 4/2004 | Johnson et al. |
| 6,723,064 B2 | 4/2004 | Babaev |
| 6,730,104 B1 | 5/2004 | Sepetka et al. |
| 6,733,517 B1 | 5/2004 | Collins |
| 6,740,104 B1 | 5/2004 | Solar et al. |
| 6,749,627 B2 | 6/2004 | Thompson et al. |
| 6,755,803 B1 | 6/2004 | Le et al. |
| 6,755,812 B2 | 6/2004 | Peterson et al. |
| 6,755,847 B2 | 6/2004 | Eskuri |
| 6,758,854 B1 | 7/2004 | Butler et al. |
| 6,761,708 B1 | 7/2004 | Chiu et al. |
| 6,764,464 B2 | 7/2004 | McGuckin, Jr. et al. |
| 6,773,448 B2 | 8/2004 | Kusleika et al. |
| 6,790,204 B2 | 9/2004 | Zadno-Azizi et al. |
| 6,824,545 B2 | 11/2004 | Sepetka et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,958,059 B2 | 10/2005 | Zadno-Azizi |
| 6,960,189 B2 | 11/2005 | Bates et al. |
| 6,972,030 B2 | 12/2005 | Lee et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,325 B1 | 4/2006 | Sullivan |
| 7,033,336 B2 | 4/2006 | Hogendijk |
| 7,033,344 B2 | 4/2006 | Imran |
| 7,048,758 B2 | 5/2006 | Boyle et al. |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,118,539 B2 | 10/2006 | Vrba et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,169,165 B2 | 1/2007 | Belef et al. |
| 7,172,621 B2 | 2/2007 | Theron |
| 7,223,253 B2 | 5/2007 | Hogendijk |
| 7,232,452 B2 | 6/2007 | Adams et al. |
| 7,242,977 B2 | 7/2007 | Partridge et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,316,678 B2 | 1/2008 | Nash et al. |
| 7,367,982 B2 | 5/2008 | Nash et al. |
| 7,374,560 B2 | 5/2008 | Ressemann et al. |
| 7,374,561 B2 | 5/2008 | Barbut |
| 7,381,200 B2 | 6/2008 | Katoh et al. |
| 7,384,412 B2 | 6/2008 | Coppi |
| 7,402,151 B2 | 7/2008 | Rosenman et al. |
| 7,422,579 B2 | 9/2008 | Wahr et al. |
| 7,458,980 B2 | 12/2008 | Barbut |
| 7,497,844 B2 | 3/2009 | Spear et al. |
| 7,524,303 B1 | 4/2009 | Don Michael et al. |
| 7,534,250 B2 | 5/2009 | Schaeffer et al. |
| 7,604,612 B2 | 10/2009 | Ressemann et al. |
| 7,731,683 B2 | 6/2010 | Jang et al. |
| 7,736,355 B2 | 6/2010 | Itou et al. |
| 7,766,049 B2 | 8/2010 | Miller et al. |

(56) References Cited

U.S. PATENT DOCUMENTS

| | | |
|---|---|---|
| 7,766,820 B2 | 8/2010 | Core |
| 7,806,906 B2 | 10/2010 | Don Michael |
| 7,815,626 B1 | 10/2010 | McFadden et al. |
| 7,842,065 B2 | 11/2010 | Belef et al. |
| 7,850,654 B2 | 12/2010 | Belhe et al. |
| 7,854,746 B2 | 12/2010 | Dorn et al. |
| 7,867,216 B2 | 1/2011 | Wahr et al. |
| 7,905,856 B2 | 3/2011 | McGuckin, Jr. et al. |
| 7,905,877 B1 | 3/2011 | Jimenez et al. |
| 7,909,812 B2 | 3/2011 | Jansen et al. |
| 7,927,309 B2 | 4/2011 | Palm |
| 7,927,347 B2 | 4/2011 | Hogendijk et al. |
| 7,967,789 B2 | 6/2011 | Solar et al. |
| 7,972,294 B2 | 7/2011 | Nash et al. |
| 7,972,308 B2 | 7/2011 | Putz |
| 7,998,104 B2 | 8/2011 | Chang |
| 8,021,351 B2 | 9/2011 | Boldenow et al. |
| 8,029,533 B2 | 10/2011 | Bagaoisan et al. |
| 8,043,279 B2 | 10/2011 | Hisamatsu et al. |
| 8,048,032 B2 | 11/2011 | Root et al. |
| 8,052,640 B2 | 11/2011 | Fiorella et al. |
| 8,066,757 B2 | 11/2011 | Ferrera et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,172,831 B2 | 5/2012 | Webler, Jr. |
| 8,181,324 B2 | 5/2012 | McFadden et al. |
| 8,221,348 B2 | 7/2012 | Hackett et al. |
| 8,231,600 B2 | 7/2012 | von Hoffmann |
| 8,251,978 B2 | 8/2012 | Nash et al. |
| 8,252,010 B1 | 8/2012 | Raju et al. |
| 8,292,850 B2 | 10/2012 | Root et al. |
| 8,343,089 B2 | 1/2013 | Chang |
| 8,414,516 B2 | 4/2013 | Chang |
| 8,425,549 B2 | 4/2013 | Lenker et al. |
| 8,465,456 B2 | 6/2013 | Stivland |
| 8,523,801 B2 | 9/2013 | Nash et al. |
| 8,535,272 B2 | 9/2013 | Wang et al. |
| 8,545,552 B2 | 10/2013 | Garrison et al. |
| 8,574,245 B2 | 11/2013 | Garrison et al. |
| 8,690,907 B1 | 4/2014 | Janardhan et al. |
| 8,708,954 B2 | 4/2014 | Webler |
| 8,801,670 B2 | 8/2014 | Drontle et al. |
| 8,870,805 B2 | 10/2014 | Chang |
| 8,876,776 B2 | 11/2014 | Kassab et al. |
| RE45,380 E | 2/2015 | Root et al. |
| 8,961,549 B2 | 2/2015 | Conn |
| 8,996,095 B2 | 3/2015 | Anderson et al. |
| 9,034,007 B2 | 5/2015 | Janardhan |
| 9,144,662 B2 | 9/2015 | Di Caprio et al. |
| RE45,760 E | 10/2015 | Root et al. |
| RE45,776 E | 10/2015 | Root et al. |
| 9,211,132 B2 | 12/2015 | Bowman |
| 9,220,562 B2 | 12/2015 | Brannan et al. |
| 9,233,230 B2 | 1/2016 | Puhasmagi et al. |
| RE46,116 E | 8/2016 | Root et al. |
| 9,764,118 B2 | 9/2017 | Anderson et al. |
| 9,820,761 B2 | 11/2017 | Garrison et al. |
| 10,058,339 B2 | 8/2018 | Galdonik et al. |
| 10,456,552 B2 | 10/2019 | Goyal |
| 2001/0044598 A1 | 11/2001 | Parodi |
| 2001/0049486 A1 | 12/2001 | Evans et al. |
| 2001/0049517 A1 | 12/2001 | Zadno-Azizi et al. |
| 2002/0087076 A1 | 7/2002 | Meguro et al. |
| 2002/0087119 A1 | 7/2002 | Parodi |
| 2002/0128679 A1 | 9/2002 | Turovskiy et al. |
| 2002/0133111 A1 | 9/2002 | Shadduck |
| 2002/0151922 A1 | 10/2002 | Hogendijk et al. |
| 2002/0156455 A1 | 10/2002 | Barbut |
| 2002/0156460 A1 | 10/2002 | Ye et al. |
| 2002/0165598 A1 | 11/2002 | Wahr et al. |
| 2002/0173785 A1 | 11/2002 | Spear et al. |
| 2002/0173815 A1 | 11/2002 | Hogendijk et al. |
| 2002/0183783 A1 | 12/2002 | Shadduck |
| 2003/0040762 A1 | 2/2003 | Dorros et al. |
| 2003/0050600 A1 | 3/2003 | Ressemann et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0186203 A1 | 10/2003 | Aboud |
| 2003/0212304 A1 | 11/2003 | Lattouf |
| 2003/0212384 A1 | 11/2003 | Hayden |
| 2003/0233038 A1 | 12/2003 | Hassett |
| 2004/0019322 A1 | 1/2004 | Hoffmann |
| 2004/0059243 A1 | 3/2004 | Flores et al. |
| 2004/0116878 A1 | 6/2004 | Byrd et al. |
| 2004/0133232 A1 | 7/2004 | Rosenbluth et al. |
| 2004/0138608 A1 | 7/2004 | Barbut et al. |
| 2004/0210194 A1 | 10/2004 | Bonnette et al. |
| 2005/0004553 A1 | 1/2005 | Douk |
| 2005/0065467 A1 | 3/2005 | Pudelko et al. |
| 2005/0090802 A1 | 4/2005 | Connors et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0209559 A1 | 9/2005 | Thornton et al. |
| 2005/0273051 A1 | 12/2005 | Coppi |
| 2006/0020165 A1 | 1/2006 | Adams |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0079787 A1 | 4/2006 | Whiting et al. |
| 2006/0089618 A1 | 4/2006 | McFerran et al. |
| 2006/0135961 A1 | 6/2006 | Rosenman et al. |
| 2006/0200191 A1 | 9/2006 | Zadno-Azizi |
| 2006/0258987 A1 | 11/2006 | Lentz et al. |
| 2006/0271098 A1 | 11/2006 | Peacock |
| 2007/0021778 A1 | 1/2007 | Carly |
| 2007/0073264 A1 | 3/2007 | Stedman et al. |
| 2007/0106211 A1 | 5/2007 | Provost-Tine et al. |
| 2007/0173784 A1 | 7/2007 | Johansson et al. |
| 2007/0185522 A1 | 8/2007 | Davies et al. |
| 2007/0197956 A1 | 8/2007 | Le et al. |
| 2007/0198028 A1 | 8/2007 | Miloslavski et al. |
| 2007/0198049 A1 | 8/2007 | Barbut |
| 2007/0208302 A1 | 9/2007 | Webster et al. |
| 2007/0260219 A1 | 11/2007 | Root et al. |
| 2008/0058839 A1 | 3/2008 | Nobles et al. |
| 2008/0082107 A1 | 4/2008 | Miller et al. |
| 2008/0140010 A1 | 6/2008 | Kennedy et al. |
| 2008/0177245 A1 | 7/2008 | Mesallum |
| 2008/0183128 A1 | 7/2008 | Morriss et al. |
| 2008/0200946 A1 | 8/2008 | Braun et al. |
| 2008/0243222 A1 | 10/2008 | Schafersman et al. |
| 2008/0294111 A1 | 11/2008 | Tal et al. |
| 2009/0018455 A1 | 1/2009 | Chang |
| 2009/0018525 A1 | 1/2009 | Waite et al. |
| 2009/0024072 A1 | 1/2009 | Criado et al. |
| 2009/0030400 A1 | 1/2009 | Bose et al. |
| 2009/0082800 A1 | 3/2009 | Janardhan |
| 2009/0198172 A1 | 8/2009 | Garrison et al. |
| 2009/0254166 A1* | 10/2009 | Chou .................... A61B 34/30 623/1.11 |
| 2009/0264865 A1 | 10/2009 | Kawai |
| 2009/0299393 A1 | 12/2009 | Martin et al. |
| 2010/0004607 A1* | 1/2010 | Wilson ................ A61B 17/22 604/266 |
| 2010/0030141 A1 | 2/2010 | Chermoni |
| 2010/0030186 A1 | 2/2010 | Stivland |
| 2010/0042118 A1 | 2/2010 | Garrison et al. |
| 2010/0063479 A1 | 3/2010 | Merdan et al. |
| 2010/0063480 A1 | 3/2010 | Shireman |
| 2010/0094330 A1 | 4/2010 | Barbut |
| 2010/0114017 A1 | 5/2010 | Lenker et al. |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0217276 A1* | 8/2010 | Garrison ........... A61M 25/0662 606/128 |
| 2010/0228269 A1 | 9/2010 | Garrison et al. |
| 2010/0256600 A1 | 10/2010 | Ferrera |
| 2010/0318097 A1 | 12/2010 | Ferrera et al. |

(56) References Cited

U.S. PATENT DOCUMENTS

| | | | |
|---|---|---|---|
| 2011/0009875 A1 | 1/2011 | Grandfield et al. | |
| 2011/0015482 A1 | 1/2011 | Carrillo, Jr. | |
| 2011/0034986 A1 | 2/2011 | Chou et al. | |
| 2011/0087147 A1 | 4/2011 | Garrison et al. | |
| 2011/0112567 A1* | 5/2011 | Lenker | A61M 25/0023 606/194 |
| 2011/0125181 A1 | 5/2011 | Brady et al. | |
| 2011/0152760 A1 | 6/2011 | Parker | |
| 2011/0238041 A1 | 9/2011 | Lim et al. | |
| 2011/0264133 A1 | 10/2011 | Hanlon et al. | |
| 2012/0095485 A1 | 4/2012 | Cully et al. | |
| 2012/0109044 A1 | 5/2012 | Santamore et al. | |
| 2012/0116350 A1 | 5/2012 | Strauss et al. | |
| 2012/0179097 A1 | 7/2012 | Cully et al. | |
| 2012/0310212 A1 | 12/2012 | Fischell et al. | |
| 2013/0035628 A1 | 2/2013 | Garrison et al. | |
| 2013/0116701 A1 | 5/2013 | Wang et al. | |
| 2013/0165873 A1 | 6/2013 | Morriss et al. | |
| 2013/0184735 A1 | 7/2013 | Fischell et al. | |
| 2013/0197621 A1 | 8/2013 | Ryan et al. | |
| 2013/0226276 A1 | 8/2013 | Newell et al. | |
| 2013/0281788 A1* | 10/2013 | Garrison | A61M 25/0662 600/208 |
| 2014/0025043 A1 | 1/2014 | Wang et al. | |
| 2014/0046297 A1 | 2/2014 | Shimada et al. | |
| 2014/0155783 A1 | 6/2014 | Starksen et al. | |
| 2014/0180246 A1 | 6/2014 | Comerota et al. | |
| 2014/0236120 A1 | 8/2014 | Tsai et al. | |
| 2014/0257018 A1 | 9/2014 | Farnan | |
| 2014/0257186 A1 | 9/2014 | Kerr | |
| 2014/0296769 A1 | 10/2014 | Hyde et al. | |
| 2014/0296868 A1 | 10/2014 | Garrison et al. | |
| 2014/0371709 A1 | 12/2014 | Allen et al. | |
| 2015/0173782 A1 | 6/2015 | Garrison et al. | |
| 2015/0196210 A1 | 7/2015 | McCaffrey et al. | |
| 2015/0265802 A1* | 9/2015 | Fukuoka | A61M 25/0074 604/508 |
| 2016/0008025 A1 | 1/2016 | Gupta et al. | |
| 2016/0015935 A1 | 1/2016 | Chan et al. | |
| 2019/0008534 A1 | 1/2019 | Garrison et al. | |
| 2019/0046218 A1 | 2/2019 | Garrison et al. | |

FOREIGN PATENT DOCUMENTS

| | | |
|---|---|---|
| EP | 0427429 A2 | 5/1991 |
| EP | 1440663 A1 | 7/2004 |
| EP | 1639951 A1 | 3/2006 |
| JP | H11-146883 A | 6/1999 |
| JP | 2003-521286 A | 7/2003 |
| JP | 2003-522560 A | 7/2003 |
| JP | 2005-500138 A | 1/2005 |
| JP | 2005-523123 A | 8/2005 |
| WO | WO-95/05209 A1 | 2/1995 |
| WO | WO-98/38930 A1 | 9/1998 |
| WO | WO-99/45835 A2 | 9/1999 |
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |
| WO | WO-2010/075445 A1 | 7/2010 |
| WO | WO-2010/075565 A2 | 7/2010 |
| WO | WO-2012/047803 A3 | 4/2012 |
| WO | WO-2015/042368 A2 | 3/2015 |

OTHER PUBLICATIONS

U.S. Appl. No. 15/699,401, filed Sep. 8, 2017, US 2017-0368309.
U.S. Appl. No. 15/727,373, filed Oct. 6, 2017, US 2018-0028205.
U.S. Appl. No. 15/747,089, filed Jan. 23, 2018, US 2018-0242978.
U.S. Appl. No. 15/866,012, filed Jan. 9, 2018, US 2018-0193042.
U.S. Appl. No. 15/875,214, filed Jan. 19, 2018, US 2018-0361114.
U.S. Appl. No. 15/875,342, filed Jan. 19, 2018, US 2018-0207399.
U.S. Appl. No. 16/117,741, filed Aug. 30, 2018, US 2019-0008534.
U.S. Appl. No. 16/117,753, filed Aug. 30, 2018, US 2019-0046218.
U.S. Appl. No. 16/414,532, filed May 16, 2019, US 2019-0351182.
U.S. Appl. No. 16/530,845, filed Aug. 2, 2019, US 2020-0023160.
U.S. Appl. No. 16/543,215, filed Aug. 16, 2019, US 2019-0366042.
U.S. Appl. No. 16/543,226, filed Aug. 16, 2019, US 2019-0366043.
U.S. Appl. No. 16/584,220, filed Sep. 26, 2019, US 2020-0016369.
U.S. Appl. No. 16/584,351, filed Sep. 26, 2019, US 2020-0038628.
U.S. Appl. No. 16/596,531, filed Oct. 8, 2019, US 2020-0046939.
U.S. Appl. No. 16/596,535, filed Oct. 8, 2019, US 2020-0046940.
PCT/US2019/032694, May 16, 2019, WO 2019/222518.
"Asahi Fubuki Catheter Dilator Kit." Asahi-Intecc USA Medical. 2017. Web. Accessed Oct. 2, 2017. 3 pages. www.asahi-inteccusa-medical.com/medical-product/fubuki-dilator-kit/. Accessed Oct. 2, 2017.
"2012 Buyer's Guide: Microcatheters." Endovascular Today, 2012, pp. 48-51.
"2017 Buyer's Guide: Microcatheters." Endovascular Today, http://evtoday.com/buyers-guide/chart.asp?id=25. Accessed on Oct. 10, 2017. 11 pages.
Adami, M.D., et al., (2002) "Use of the Parodi Anti-Embolism System in Carotid Stenting: Italian Trial Results" J Endovasc Ther 9:147-154.
Alexandrescu et al. (2006) "Filter-protected carotid stenting via a minimal cervical access with transitory aspirated reversed flow during initial passage of the target lesion." J. Endovasc. Ther. 13(2):196-204.
Alvarez et al. (2008). "Transcervical carotid stenting with flow reversal is safe in octogenarians: A preliminary safety study" J. Vasc. Surg. 47:96-100.
Bates M.D., et al. "Reversal of the Direction of Internal Carotid Artery Blood Flow by Occlusion of the Common and External Carotid Arteries in a Swine Model" Catherization and Cardiovascular Intervention 60:270-275 (2003).
Bates, M.D., et al. (2004) "Internal Carotid Artery Flow Arrest/Reversal Cerebral Protection Techniques" The West Virginal Medical Journal, vol. 99:60-63.
Bergeron et al. (1999). "Percutaneous stenting of the internal carotid artery: the European CAST I Study" J. Endovasc. Surg. 6:155-159.
Bergeron et al. (2008) MEET Presentation, Cannes, French Riviera "Why I do not use routine femoral access for CAS." 12 pages.
Bergeron P. et al. (1996) "Recurrent Carotid Disease: Will Stents be an alternative to surgery?" J Endovasc Surg; 3: 76-79.
Bourekas, E. C., A. P. Slivka, et al. (2004). "Intraarterial thrombolytic therapy within 3 hours of the onset of stroke." Neurosurgery 54(1): 39-44; discussion 44-6.
Chang, D.W., et al, "A new approach to carotid angioplasty and stenting with transcervical occlusion and protective shunting: Why it may be a better carotid artery intervention" (J Vasc Surg 2004; 39:994-1002.).
Chang, M.D., "Carotid Angioplasty and Stenting Using Transcervical Occlusion and Protective Shunting Via a Mini Incision in the Neck: A New Technique for Difficult Femoral Access or Filter Placement May Be the Better Carotid Artery Intervention" 30th Global: Vascular and Endovascular Issues, Techniques and Horizons. Nov. 22-23, 2003, XXVII 6.1-XXVII 6.2.
Cohen et al., "A reappraisal of the common carotid artery as an access site in interventional procedures for acute stroke therapies", Case Reports, Journal of Clinical Neuroscience 19 (2012) pp. 323-326.
Coppi et al. (2005). "PRIAMUS Proximal flow blockage cerebral protection during carotid stenting: Results from a multicenter Italian regiStry" J. Cardiovasc. Surg. 46:219-227.
Criado et al. (1997) "Evolving indications for and early results of carotid artery stenting" Am. J. Surg.; 174:111-114.

(56) References Cited

OTHER PUBLICATIONS

Criado et al. (2004). "Transcervical carotid artery angioplasty and stenting with carotid flow reversal: Surgical technique" J. Vasc. Surg. 18:257-261.

Criado et al. (2004). "Transcervical carotid stenting with internal carotid artery flow reversal: Feasibility and preliminary results" J. Vasc. Surg. 40:476-483.

Criado, et al. (2007). "Transcervical carotid stenting with carotid artery flow reversal: 3-year follow-up of 103 stents." J Vasc Surg 46(5): 864-9.

Criado, F.J., et al., Access strategies for carotid artery intervention. J Invasive Cardiol, 2000. 12(1): p. 61-68.

Criado, M.D., et al. (2004) "Carotid angioplasty with internal carotid artery flow reversal is well tolerated in the awake patient" Journal of Vascular Surgery, 40(1):92-7.

Diederich et al. (2004) "First Clinical experiences with an endovascular clamping system for neuroprotection during carotid stenting." *Eur. J. Vasc. Endovasc. Surg.* 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.

Farooq, Vasim et al. "The Use of a Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.

Feldtman, R. W., C. J. Buckley, et al. (2006). "How I do it: cervical access for carotid artery stenting." Am J Surg 192(6): 779-81.

Fiorella, D., M. Kelly, et al. (2008). "Endovascular Treatment of Cerebral Aneurysms." Endovascular Today June. pp. 53-64.

Frazee, J. G. and X. Luo (1999). "Retrograde transvenous perfusion." Crit Care Clin 15(4): 777-88, vii.

Frazee, J. G., X. Luo, et al. (1998). "Retrograde transvenous neuroperfusion: a back door treatment for stroke." Stroke 29(9): 1912-6.

Goldstein "Acute Ischemic Stroke Treatment in 2007" *Circ* 116:1504-1514 (2007).

Goyal, M. et al. (Mar. 12, 2015, e-published Feb. 11, 2015). "Randomized Assessment of Rapid Endovascular Treatment of Ischemic Stroke." *N Engl J Med*, 372(11):1019-1030.

Gray et al. (2007) "The Capture registry: Results of carotid stenting with embolic protection in the post approval setting" *Cath. Cardovasc. Interven.* 69:341-348.

Henry et al. (1999) "Carotid stenting with cerebral protection: First clinical experience using the PercuSurge GuardWire System" *J. Endovasc. Surg.* 6:321-331.

Koebbe, C. J., E. Veznedaroglu, et al. (2006). "Endovascular management of intracranial aneurysms: current experience and future advances." Neurosurgery 59(5 Suppl 3): S93-102; discussion S3-13.

Lin et al. (2005) "Protected carotid artery stenting and angioplasty via transfemoral versus transcervical approaches" Vasc. Endovasc. Surg. 39(6):499-503.

Lo et al. (2005) "Advantages and indications of transcervical carotid artery stenting with carotid flow reversal" J. Cardovasc. Surg (Torino). 46(3):229-239.

Luebke, T et al. (2007) "Meta-analysis of randomized trials comparing carotid endarterectomy and endovascular treatment" *Eur. J. Vasc. Endovasc. Surg.* 34:470-479.

MacDonald, S. (2006) "Is there any evidence that cerebral protection is beneficial?" *J. Cardiovasc. Surg.* 47:127-36.

Mas et al. (2006) "Endarterectomy versus stenting in patients with symptomatic severe carotid stenosis" *NEJM* 355:1660-71.

Matas et al. (2007). "Transcervical carotid stenting with flow reversal protection: Experience in high-risk patients" J. Vasc. Surg. 46:49-54.

Momapresn (AET) 2002 Biamino, G; MO.MA as a distal protective device, University of Leipzig—Heart Center Department of Clinical and Interventional; Angiology Leipzig, Germany; 2002. 37 pages.

Nesbit, G. M., G. Luh, et al. (2004). "New and future endovascular treatment strategies for acute ischemic stroke." J Vasc Interv Radiol 15(1 Pt 2): S103-10.

Nii, K., K. Kazekawa, et al. (2006). "Direct carotid puncture for the endovascular treatment of anterior circulation aneurysms." AJNR Am J Neuroradiol 27(7): 1502-4.

Ohki, M.D., et al., "Efficacy of a proximal occlusion catheter with reversal of flow in the prevention of embolic events during carotid artery stenting: An experimental analysis" (J Vasc Surg 2001; 33:504-9).

Ouriel, K., R. K. Greenberg, et al. (2001). "Hemodynamic conditions at the carotid bifurcation during protective common carotid occlusion." J Vasc Surg 34(4): 577-80.

Parodi (2005). "Is flow reversal the best method of protection during carotid stenting?" J Endovasc. Ther. 12:166-170.

Parodi et al. (2000). "Initial evaluation of carotid angioplasty and stenting with three different cerebral protection devices" J. Vasc. Surg. 32:1127-1136.

Parodi, J. C., L. M. Ferreira, et al. (2005). "Cerebral protection during carotid stenting using flow reversal." J Vasc Surg 41(3): 416-22.

Pena, Carlos. "Letter to Sequent Medical Inc Re: K150894, Trade/Device Name: VIA™ 21 Microcatheter." Department of Health & Human Services, Aug. 28, 2015, 14 pages.

Perez-Arjona, E. A., Z. DelProsto, et al. (2004). "Direct percutaneous carotid artery stenting with distal protection: technical case report." Neurol Res 26(3): 338-41.

Pipinos et al. (2005). "Transcervical approach with protective flow reversal for carotid angioplasty and stenting" J. Endovasc. Ther. 12:446-453.

Pipinos et al. (2006). "Transcervical carotid stenting with flow reversal for neuroprotection: Technique, results, advantages, and limitations" 14(5):245-255.

Powers, W.J., et al. (2015, e-published online before print Jun. 29, 2015). "2015 AHA/ASA Focused Update of the 2013 Guidelines for the Early Management of Patients With Acute Ischemic Stroke Regarding Endovascular Treatment: A Guideline for Healthcare Professionals From the American Heart Association/American Stroke Association Powers et al. on behalf of the American Heart Association Stroke Council Stroke." *Stroke*. 46:3020-3035.

Reekers, J. A. (1998). "A balloon protection sheath to prevent peripheral embolization during aortoiliac endovascular procedures." Cardiovasc Intervent Radiol 21(5): 431-3.

Reimers et al. (2005). "Proximal endovascular flow blockage for cerebral protection during carotid artery stenting: Results froma prospective multicenter registry" J. Endovasc. Ther. 12:156-165.

Request for Ex Parte Reexamination Transmittal Form and Request for Ex Parte Reexamination pursuant to 37 CFR 1.150 of now U.S. Pat. No. 9,820,761 issued Nov. 21, 2017. Request filed May 11, 2018 and assigned U.S. Appl. No. 90/014,136. 35 pages.

Ribo et al. (2006). "Transcranial doppler monitoring of transcervical carotid stenting with flow reversal protection: a novel carotid revascularization technique" 37:2846-2849 (originally published online Sep. 28, 2006).

Ribo, M., C. Molina, et al. (2008). "Buying Time for Recanalization in Acute Stroke: Arterial Blood Infusion Beyond the Occluding Clot as a Neuroprotective Strategy." J Neuroimaging. 4 pages.

Ross, I. B. and G. D. Luzardo (2006). "Direct access to the carotid circulation by cut down for endovascular neuro-interventions." Surg Neurol 65(2): 207-11; discussion 211.

Saver, J.L. et al. (Jun. 11, 2015, e-published Apr. 17, 2015). "Stent-Retriever Thrombectomy after Intravenous t-PA vs. t-PA Alone in Stroke." *N Engl J Med*, 372(24):2285-2295.

Stecker et al., (2002). "Stent placement in common carotid and internal carotid artery stenoses with use of an open transcervical approach in a patient with previous endarterectomy." J. Vasc. Interv. Radiol. 13:413-417.

Stejskal, et al., "Experience of 500 Cases of Neurophysiological Monitoring in Carotid Endarterectomy", Acta Neurochir, 2007, 149:681-689.

(56) References Cited

OTHER PUBLICATIONS

Theron, et al. "New Triple Coaxial Catheter System for Carotid Angioplasty with Cerebral Protection" AJNR 11:869-874, Sep.-Oct. 1990 0195-6108/90/1106-0869 @ American Society of Neurology.
Zuckerman, Bram. "Letter to Cathera Inc: Re K151638, Trade/Device Name: Phenom™ Catheters." Department of Health & Human Services, Nov. 13, 2015, 6 pages.

* cited by examiner

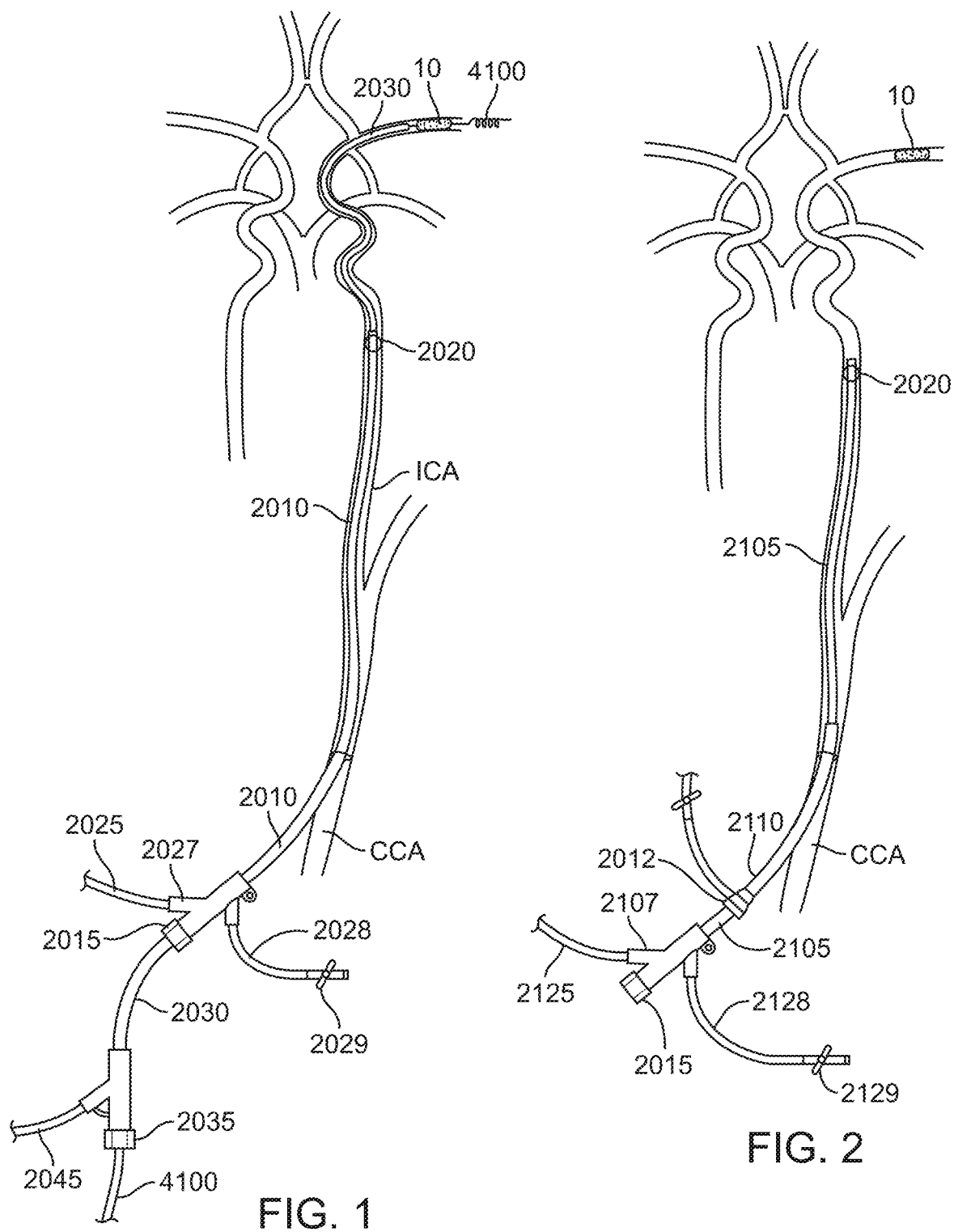

METHODS AND SYSTEMS FOR TREATMENT OF ACUTE ISCHEMIC STROKE

CROSS-REFERENCES TO RELATED APPLICATIONS

This application is a continuation of co-pending U.S. patent application Ser. No. 16/117,753, filed Aug. 30, 2018, which is a continuation of U.S. patent application Ser. No. 13/566,451, filed Aug. 3, 2012, which claims priority of the following U.S. Provisional patent applications: (1) U.S. Provisional Patent Application Ser. No. 61/515,736, filed on Aug. 5, 2011; (2) U.S. Provisional Patent Application Ser. No. 61/543,019, filed on Oct. 4, 2011; (3) U.S. Provisional Patent Application Ser. No. 61/547,597, filed on Oct. 14, 2011; (4) U.S. Provisional Patent Application Ser. No. 61/579,581, filed on Dec. 22, 2011. The disclosures of the patent applications are hereby incorporated by reference in their entirety.

BACKGROUND

The present disclosure relates generally to medical methods and devices for the treatment of acute ischemic stroke. More particularly, the present disclosure relates to methods and systems for transcervical access of the cerebral arterial vasculature and treatment of cerebral occlusions.

Acute ischemic stroke is the sudden blockage of adequate blood flow to a section of the brain, usually caused by thrombus or other emboli lodging or forming in one of the blood vessels supplying the brain. If this blockage is not quickly resolved, the ischemia may lead to permanent neurologic deficit or death. The timeframe for effective treatment of stroke is within 3 hours for intravenous (IV) thrombolytic therapy and 6 hours for site-directed intra-arterial thrombolytic therapy or interventional recanalization of a blocked cerebral artery. Reperfusing the ischemic brain after this time period has no overall benefit to the patient, and may in fact cause harm due to the increased risk of intracranial hemorrhage from fibrinolytic use. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death in the United States.

Endovascular treatment of acute stroke is comprised of either the intra-arterial administration of thrombolytic drugs such as recombinant tissue plasminogen activator (rtPA), or mechanical removal of the blockage, or often a combination of the two. As mentioned above, these interventional treatments must occur within hours of the onset of symptoms. Both intra-arterial (IA) thrombolytic therapy and interventional thrombectomy involve accessing the blocked cerebral artery. Like IV thrombolytic therapy, IA thrombolytic therapy has the limitation in that it may take several hours of infusion to effectively dissolve the clot.

Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Frank suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons, stents and temporary stents have been used to create a patent lumen through the clot when clot removal or dissolution was not possible. Temporary stents, sometimes referred to as stentrievers or revascularization devices, may also be utilized to remove or retrieve clot as well as restore flow to the vessel.

Some Exemplary Issues with Current Technology

Interventions in the cerebral vasculature often have special access challenges. Most neurointerventional procedures use a transfemoral access to the carotid or vertebral artery and thence to the target cerebral artery. However, this access route is often tortuous and may contain stenosis plaque material in the aortic arch and carotid and brachiocephalic vessel origins, presenting a risk of embolic complications during the access portion of the procedure. In addition, the cerebral vessels are usually more delicate and prone to perforation than coronary or other peripheral vasculature. In recent years, interventional devices such as wires, guide catheters, stents and balloon catheters, have all been scaled down and been made more flexible to better perform in the neurovascular anatomy. However, many neurointerventional procedures remain either more difficult or impossible because of device access challenges. In the setting of acute ischemic stroke where "time is brain," these extra difficulties have a significant clinical impact.

Another challenge of neurointerventions is the risk of cerebral emboli. During the effort to remove or dissolve clot blockages in the cerebral artery, there is a significant risk of thrombus fragmentation creating embolic particles which can migrate downstream and compromise cerebral perfusion, leading to neurologic events. In carotid artery stenting procedures CAS, embolic protection devices and systems are commonly used to reduce the risk of embolic material from entering the cerebral vasculature. The types of devices include intravascular filters, and reverse flow or static flow systems. Unfortunately, because of the delicate anatomy and access challenges as well as the need for rapid intervention, these embolic protection systems are not used in interventional treatment of acute ischemic stroke. Some of the current mechanical clot retrieval procedures use aspiration as a means to reduce the risk of emboli and facilitate the removal of the clot. For example, the MERCI Retrieval System recommends attaching a large syringe to the guide catheter, and then blocking the proximal artery and aspirating the guide catheter during pull back of the clot into the guide. However, this step requires a second operator, may require an interruption of aspiration if the syringe needs to be emptied and reattached, and does not control the rate or timing of aspiration. This control may be important in cases where there is some question of patient tolerance to reverse flow. Furthermore, there is no protection against embolic debris during the initial crossing of the clot with the microcatheter and deployment of the retrieval device. Aspiration systems such as the Penumbra System utilize catheters which aspirate at the face of the clot while a separate component is used to mechanically break up the clot. This system is limited and in the level of aspiration possible with current catheter designs, and in some cases by the ability to bring larger catheters to the location of the clot.

One severe drawback to current acute stroke interventions is the amount of time required to restore blood perfusion to the brain, which can be broken down to time required to access to the blocked cerebral artery, and time required to restore flow through the occlusion. Restoration of flow, either through thrombolytic therapy, mechanical thrombectomy, or other means, often takes hours during which time brain tissue is deprived of adequate oxygen. During this period, there is a risk of permanent injury to the brain tissue. Means to shorten the procedure time, and/or to provide oxygen to the brain tissue during the procedure, would reduce this risk.

SUMMARY

Disclosed are methods and devices that enable safe, rapid and relatively short and straight transcervical access to the cerebral arteries to treat acute ischemic stroke. The methods and devices include distal catheters and devices to remove the occlusion. Methods and devices are also included to provide aspiration and passive flow reversal for the purpose of facilitating removal of the occlusion as well as minimizing distal emboli. The system offers the user a degree of flow control so as to address the specific hemodynamic requirements of the cerebral vasculature. The disclosed methods and devices also include methods and devices to protect the cerebral penumbra during the procedure to minimize injury to brain. In addition, the disclosed methods and devices provide a way to securely close the access site in the carotid artery to avoid the potentially devastating consequences of a transcervical hematoma.

In one aspect, there is disclosed a system of devices for treating an occlusion in a cerebral artery of a patient, comprising: a transcervical access sheath adapted to be introduced into a common carotid artery via an opening directly in the artery, the opening being positioned above the patient's clavicle and below a bifurcation location where the patient's common carotid artery bifurcates into an internal carotid artery and external carotid artery, wherein the transcervical access sheath has an internal lumen; a distal catheter sized and shaped to be inserted axially through the internal lumen of the transcervical access sheath such that the distal catheter can be inserted into a cerebral artery via the transcervical access sheath, wherein the distal catheter has an internal lumen defined by an inner diameter; an elongated inner member sized and shaped to be inserted axially through the lumen of the transcervical access sheath, wherein the inner member has an internal lumen; and a guidewire configured to be inserted into the cerebral artery via internal lumen of the inner member; wherein the inner member has an outer diameter configured to form a smooth transition between the inner diameter of the distal catheter and the outer diameter of the guidewire.

In another aspect, there is disclosed a system of devices for treating an occlusion in a cerebral artery of a patient, comprising: a transcervical access sheath adapted to be introduced into a common carotid artery via an opening directly in the artery, the opening being positioned above the patient's clavicle and below a bifurcation location where the patient's common carotid artery bifurcates into an internal carotid artery and external carotid artery, wherein the transcervical access sheath has an internal lumen; and a distal catheter sized and shaped to be inserted axially through the internal lumen of the transcervical access sheath such that the distal catheter can be inserted into a cerebral artery via the transcervical access sheath, wherein the distal catheter has a first internal lumen and a smaller, second internal lumen, wherein a distal-most portion of the second internal lumen is positioned inside an extension that protrudes distally past a distal opening formed by the first lumen.

In another aspect, there is disclosed a system of devices for treating an occlusion in a cerebral artery of a patient, comprising: a transcervical introducer sheath adapted to be introduced into a common carotid artery via an opening directly in the artery, the opening being positioned above the patient's clavicle and below a bifurcation location where the patient's common carotid artery bifurcates into an internal carotid artery and external carotid artery, wherein the transcervical introducer sheath has an internal lumen; a flow line connected to the introducer sheath, wherein the flow line provides a pathway for blood to flow from the introducer sheath to a return site; a hemostasis valve on a proximal region of the introducer sheath that provides access to the internal lumen of the introducer sheath while preventing blood loss; and a guide catheter sized and shaped to be inserted through the hemostasis valve into the internal lumen of the introducer sheath such that the guide catheter can provide access to a cerebral artery via an internal of the guide catheter.

In another aspect, there is disclosed a method of treating an occlusion in a cerebral artery, comprising: forming an incision in common carotid artery; inserting a transcervical access sheath through the incision into the common carotid artery and deploying a distal end of the sheath in the common or internal carotid artery, wherein the access sheath has an internal lumen; inserting a first distal catheter into the internal lumen of the access sheath; positioning a distal end of the first distal catheter in the cerebral artery adjacent the occlusion; aspirating through the first distal catheter to capture the occlusion at the distal end of the first distal catheter; and retracting the distal end of the first distal catheter into the access sheath to pull the occlusion into the access sheath.

Other features and advantages should be apparent from the following description of various embodiments, which illustrate, by way of example, the principles of the invention.

BRIEF DESCRIPTION OF THE DRAWINGS

FIG. 1 illustrates an exemplary embodiment of a system of devices for transcervical access and treatment of acute ischemic stroke showing a balloon-tipped arterial access device inserted directly into the carotid artery, a distal catheter, a thrombectomy device.

FIG. 2 illustrates an alternate embodiment wherein the arterial access device is inserted into the carotid artery through a separate introducer sheath.

DETAILED DESCRIPTION

Figure 3:
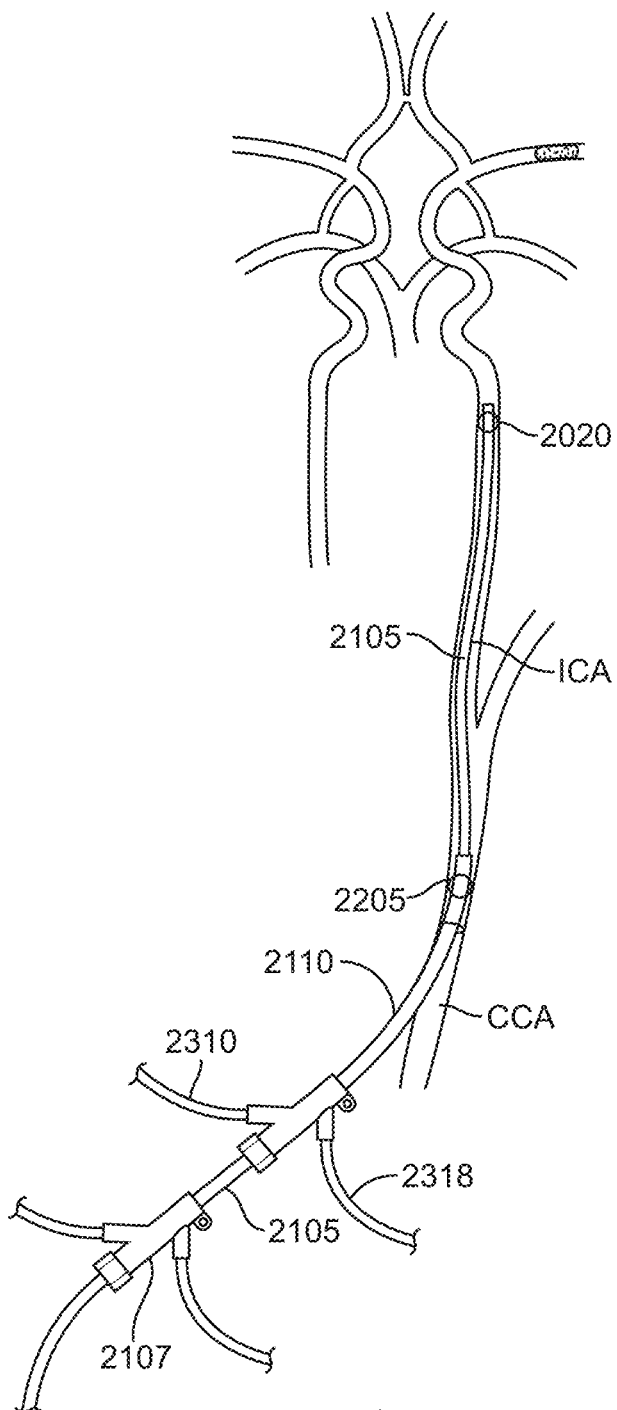
FIG. 3 illustrates an embodiment in which the introducer sheath has an occlusion balloon and a connection to a flow line.

Described herein are methods and devices that enable safe, rapid and relatively short and straight transcervical access to the carotid arteries and cerebral vasculature for the introduction of interventional devices for treating ischemic stroke. Transcervical access provides a short length and non-tortuous pathway from the vascular access point to the target cerebral vascular treatment site, thereby easing the time and difficulty of the procedure, compared for example to a transfemoral approach. Additionally, this access route reduces the risk of emboli generation from navigation of diseased, angulated, or tortuous aortic arch or carotid artery anatomy.

FIG. 1 shows a system of devices for accessing the common carotid artery CCA via a transcervical approach and for delivering devices to the cerebral vasculature. The system includes an arterial access device 2010 (sometimes referred to as an arterial access sheath), such as a sheath, having an internal lumen and a port 2015. The arterial access device 2010 is sized and shaped to be inserted into the common carotid artery via a transcervical incision or puncture and deployed into a position that provides access to the cerebral vasculature, for example the common or internal carotid artery. The port 2015 provides access to the arterial access device's internal lumen, which is configured for introducing additional devices into the cerebral vasculature via the arterial access device 2010.

In an embodiment, transcervical access to the common carotid artery directly with the arterial access device 2010 is achieved percutaneously via an incision or puncture in the skin. In an alternate embodiment, the arterial access device 2010 accesses the common carotid artery CCA via a direct surgical cut down to the carotid artery. In another embodiment, the arterial access device provides access to the basilar artery BA or posterior cerebral arteries PCA via a cut down incision to in the vertebral artery or a percutaneous puncture of the vertebral artery for access to occlusions in the posterior cerebral vasculature such as the posterior cerebral artery or basilar artery. The arterial access device may include an occlusion balloon, to block antegrade flow. For entry into the common carotid artery, the arterial access device is inserted into an opening directly in the common carotid artery, the opening being positioned above the patient's clavicle and below a bifurcation location where the patient's common carotid artery bifurcates into an internal carotid artery and external carotid artery. For example, the opening may be located at distance of around 5 cm to 7 cm below a bifurcation location where the patient's common carotid artery bifurcates into an internal carotid artery and external carotid artery.

The system may also include one or more distal catheters 2030 to provide distal access and localized aspiration at a location distal of the distal-most end of the arterial access device 2010. A single distal catheter may be adequate for accessing and treating the occlusion or occlusions. A second, smaller diameter distal catheter may be inserted through the first catheter or exchanged for the first catheter if more distal access is desired and not possible with the initial distal catheter. In an embodiment, the distal catheter 2030 is configured to be inserted into the internal lumen of the arterial access device 2010 via the port 2015. The distal catheter 2030 may use a previously placed guide wire, microcatheter, or other device acting as a guide rail and support means to facilitate placement near the site of the occlusion. The distal catheter may also utilize a dilator element to facilitate placement through the vasculature over a guidewire. Once the distal catheter is positioned at or near the target site, the dilator may be removed. The distal catheter 2030 may then be used to apply aspiration to the occlusion. The catheter 2030 or dilator may also be used to deliver additional catheters and/or interventional devices to the site of the occlusion.

The methods and devices also include devices for active aspiration as well as passive retrograde flow to facilitate removal of the occlusion and/or minimize distal emboli. The system offers the user a degree of blood flow control so as to address the specific hemodynamic requirements of the cerebral vasculature. The system may include a flow controller, which allows the user to control the timing and mode of aspiration from one or more of the devices.

With reference still to FIG. 1, a thrombectomy device 4100 such as a stentriever or a coil retriever that has been configured for transcervical access may be deployed through the arterial access device to the site of the thrombotic blockage. The thrombectomy device 4100 is inserted through the arterial access device 2010 and deployed across the occlusion in the cerebral vessel via a microcatheter. If desired, a distal catheter 2030 may be used to facilitate navigation of the thrombectomy device to the site of the occluded vessel, and/or to provide aspiration at the site of the occlusion during retrieval of the clot by the thrombectomy device. The clot is retrieved by pulling back on the thrombectomy device and microcatheter in tandem into the distal catheter 2030, if used, and thence into the arterial access device 2010.

The disclosed methods and devices also include devices to protect the cerebral penumbra during the procedure to minimize injury to the brain. A distal perfusion device may be used during the procedure to provide perfusion to the brain beyond the site of the occlusion, thereby reducing the injury to the brain from lack of blood. These perfusion devices may also provide means to reduce the forward blood pressure on the occlusion in the vessel and thus assist in removing the occlusion with either aspiration, mechanical means, or both.

In addition, the disclosed methods and devices provide means to securely close the access site to the cerebral arteries to avoid the potentially devastating consequences of a transcervical hematoma. The present disclosure provides additional methods and devices.

Exemplary Embodiments Arterial Access Device

The arterial access device 2010 as shown in FIG. 1 is configured to be directly inserted into the common carotid artery CCA without use of a separate introducer sheath. In this configuration, the entry or distal tip of the device is tapered and includes a tapered dilator so as to allow smooth introduction of the device over a guide wire into the artery. The device 2010 may include an occlusion balloon 2020 which is configured to occlude the artery when inflated. In an alternate embodiment, the arterial access device 2010 does not include an occlusion balloon. The arterial access device also includes a proximal adaptor. This proximal adaptor includes a proximal port 2015 with a hemostasis valve, to allow introduction of devices while preventing or minimizing blood loss during the procedure. In an embodiment, this valve is a static seal-type passive valve. In an alternate embodiment, this valve is an adjustable-opening valve such as a Tuohy-Borst or rotating hemostasis valve (RHV). The hemostasis valve may be integral to the proximal adaptor, or may be attached separately to the proximal end of the adaptor via a Luer connection. The arterial access device 2010 may also include a connection to a flow line 2025 (or shunt) which may be connected to means for passive or active reverse flow. The flow line 2025 has an internal lumen that communicates with an internal lumen of the arterial access device 2010 for shunting blood from the arterial access device. In an embodiment, the flow line 2025 is a side arm or Y-arm 2027 that is attached to and extends from the arterial access device 2010 at a location between the distal and proximal ends of the arterial access device 2010. As shown in FIG. 1, the flow line 2025 is located distal of the location where devices enter the proximal port 2015 of the arterial access device. In an alternate embodiment, the flow line 2025 is attached to the Y-arm of a separately attached Tuohy Borst valve.

The arterial access device 2010 may also include a lumen for balloon inflation. This lumen fluidly connects the balloon to a second Y-arm on the proximal adaptor. This Y-arm is attached to a tubing 2028 which terminates in a one-way stopcock 2029. An inflation device such as a syringe may be attached to the stopcock 2029 to inflate the balloon when vascular occlusion is desired.

In an embodiment as shown in FIG. 2, the arterial access device is a guide catheter 2105 which is inserted through the proximal hemostasis valve 2012 of a separate introducer sheath 2110 into the CCA. The arterial access device also includes a proximal adaptor. This proximal adaptor includes a proximal port 2015 with a hemostasis valve, to allow introduction of devices while preventing or minimizing blood loss during the procedure. The guide catheter 2105 may include a lumen for balloon inflation. This lumen is attached to a Y-arm in the proximal adaptor, which is connected to a tubing 2128. The tubing 2128 terminates in a one-way stopcock 2129 for connection to a balloon inflation device. The guide catheter 2105 may include a second Y-arm 2107 that communicates with a flow line 2125. Introduction through the separate sheath 2110 allows removal of the guide catheter 2105 for flushing outside the patient and reinserting, or for exchanging the guide catheter 2105 with another guide catheter without removing the introducer sheath 2110, thus maintaining access to the artery via the transcervical incision. This configuration also allows repositioning of the occlusion balloon 2020 during the procedure without disturbing the arterial insertion site. The embodiment of FIG. 2 also allows removal of the arterial access device 2105 and then insertion of a vessel closure device through the introducer sheath 2110 at the conclusion of the procedure.

In a variation of this embodiment, as shown in FIG. 3, the introducer sheath 2110 includes an occlusion balloon 2205 and an inflation line and tubing 2318. The introducer sheath 2110 may also include a connection to a flow line 2310 for passive or active reverse flow, wherein passive or active reverse flow may configured as described in U.S. patent application Ser. Nos. 12/176,250 and 12/834,869, which are incorporated herein by reference. This embodiment may be useful if the patient had a carotid stenosis in addition to a cerebral artery blockage, and the user wished to treat the carotid stenosis under static or reverse flow conditions as described in the reference patent application either prior or after treating the cerebral artery blockage.

Figure 4:
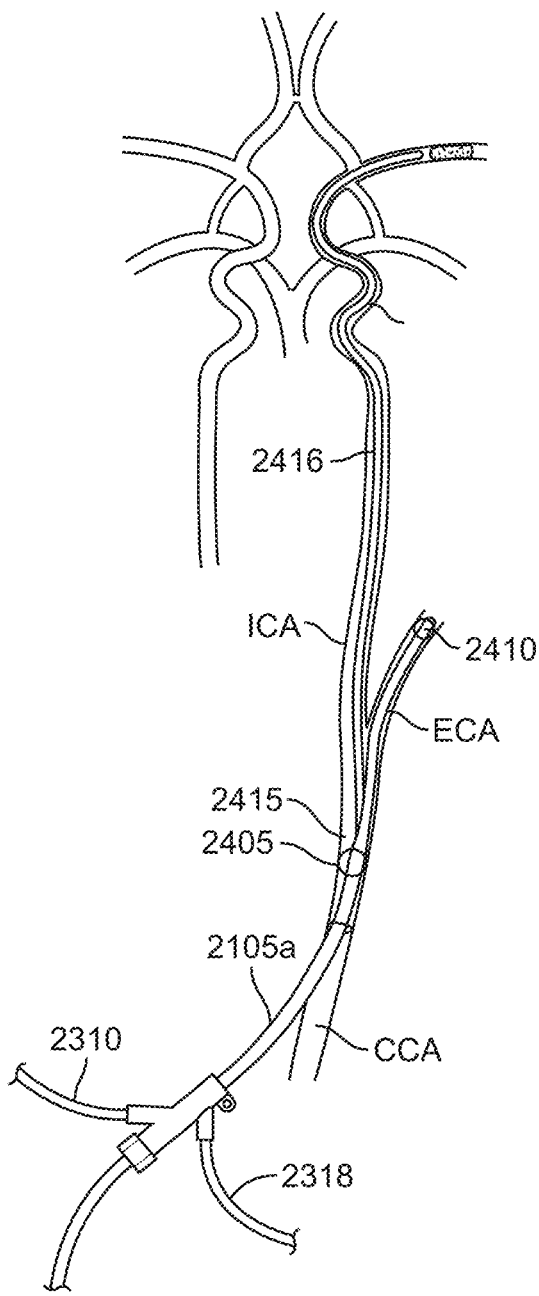
FIG. 4 illustrates an alternate embodiment of the arterial access device which has two occlusion balloons and an opening between the two balloons.

In yet another embodiment, as shown in FIG. 4, the arterial access device is a device 2105a with two occlusion balloons 2405 and 2410 and a side opening 2415 positioned between the two balloons. The distal occlusion balloon 2410 is located at or near the distal end of the arterial access device 2105a, and the proximal occlusion balloon 2405 is located between the distal end and the proximal end of the working portion of the arterial access device. The distal occlusion balloon 2410 is sized and shaped to be placed in the external carotid artery ECA and the proximal occlusion balloon 2405 is sized and shaped to be placed in the common carotid artery CCA. Such a dual balloon configuration stops flow into the internal carotid artery ICA from both the CCA and the ECA, which has an effect functionally the same as an occlusion balloon positioned in the ICA without inserting a device into the ICA. This may be advantageous if the ICA were diseased, whereby access may cause emboli to dislodge and create embolic complications, or the access to the ICA were severely tortuous and difficult to achieve, or both. The side opening 2415 in the working section of the arterial access device 2105 permits a device 2416 to be introduced via the arterial access device 2105a and inserted into the ICA via the side opening 2415 while flow is stopped or reversed, to reduce or eliminate the risk of distal emboli. This device 2416 may then be advanced to the location of the cerebral artery occlusion to treat the occlusion.

Figure 5:
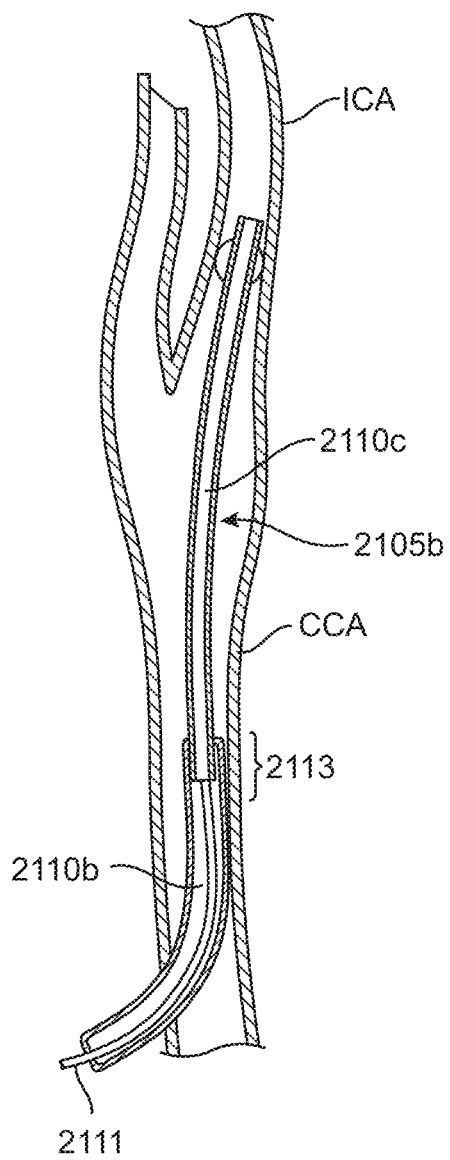
FIG. 5 illustrates an alternate embodiment of the arterial access device which includes two telescoping sections.

In yet another embodiment, as shown in FIG. 5 the arterial access device is a multi-part (such as two-part) telescoping system 2105b. The first part is an introducer sheath 2110b which is configured to be inserted transcervically into the CCA. The second part is a distal extension 2110c which is inserted through the proximal end of the introducer sheath 2110b and which extends the reach of the sheath into the ICA. The distal end of the sheath 2110b and the proximal end of the extension 2110c form a lap junction 2113 when the extension is fully inserted, such that there is a continuous lumen through the two devices. The lap junction may be variable length, such that there is some variability in the length of the combined telescoping system 2105b. The distal extension 2110c includes a tether 2111 which allows placement and retrieval of the distal extension 2110c through the sheath 2110b. In an embodiment, the distal extension includes an occlusion balloon. In this embodiment the tether include a lumen for inflation of the balloon. This tether can be connected on the proximal end to a balloon inflation device. This configuration provides the advantages of the two-part system shown in FIG. 2, without compromising the luminal area.

In an embodiment, the working portion of the arterial access device which enters the artery is constructed in two or more layers, including for example a first layer and a second layer. An inner liner is constructed from a low friction polymer such as PTFE (polytetrafluoroethylene) or FEP (fluorinated ethylene propylene) to provide a smooth surface for the advancement of devices through the inner lumen. An outer jacket material providing mechanical integrity to the liner may be constructed from materials such as Pebax, polyethylene, nylon, or the like. A third layer may consist of a reinforcement between the liner and the jacket. The purpose of the reinforcement layer is to prevent flattening or kinking of the inner lumen as the device navigates through bends in the vasculature, and provide unimpeded means for device access as well as aspiration or reverse flow. The reinforcement may be made from metal such as stainless steel, Nitinol, or the like, or stiff polymer such as PEEK. The structure may be a coil or braid, or tubing which has been laser-cut or machine-cut so as to be flexible. In addition, the device may have a radiopaque marker at the distal tip to facilitate placement of the device using fluoroscopy. In an embodiment, the working portion of the device may have a hydrophilic coating to improve the ease of advancement of the device through the vasculature.

In an embodiment, the working length of the arterial access device is of a length configured to occlude the proximal internal carotid artery when inserted from the CCA, for example 10-15 cm. In an alternate embodiment, the working length of the arterial access device is of a length suitable for closure with a vessel closure device, for example 11 cm or less. In another embodiment the device is of a length configured to occlude the distal cervical internal carotid artery (ICA) when inserted from the CCA, for example 15-25 cm. In yet another embodiment, the arterial access device is of a length configured to occlude the petrous, cavernous, or terminal portion of the ICA when inserted from the CCA, for example 20-35 cm. In this embodiment, the distal-most portion (which may have a length of about 3 to about 6 cm) of the arterial access device may be configured to be more flexible to accommodate the curvature in the petreous portion of the ICA. This additional flexibility may be achieved by using a lower durometer outer jacket material in this section. Alternately, the wall thickness of the jacket material may be reduced, and/or the density of the reinforcement layer may be varied to increase the flexibility. For example the pitch of the coil or braid may be stretched out, or the cut pattern in the tubing may be varied to be more flexible. The distal most portion of the arterial access device may also be tapered or stepped down to a smaller diameter.

The arterial access device as described above has a working length which is considerably shorter than access devices which are placed from an access location in the femoral artery. The distance from the femoral artery to the CCA is about 60-80 cm, thus devices which utilize a CCA access site may be shorter by approximately this amount. Comparable devices which are designed for femoral arterial access are typically 80-95 cm in length for devices to be deployed in the cervical ICA (e.g. the Balloon Guide, Concentric, Inc.) or 95-105 cm in length designed to access the petrous ICA (e.g. the Neuron 6F Guide, Penumbra, Inc.) The shorter lengths of access devices disclosed herein reduces the resistance to flow through the lumen of these devices and increases the rate at which aspiration may occur. In an example embodiment, the arterial access device has a length of about 10 cm to about 40 cm. In an embodiment, the length of the arterial access device is about 10.5 cm and the guide catheter has a length of about 32 cm.

The arterial access device may also include a removable proximal extension to allow the user to insert devices into the proximal port of the proximal extension and from there into the lumen of the arterial access device while minimizing exposure of the user's hands to radiation. An example of a proximal extension design is described in co-pending U.S. patent application Ser. No. 12/540,341, filed Aug. 12, 2009, which is incorporated herein by reference. U.S. patent application Ser. No. 12/633,730, U.S. patent application Ser. No. 12/645,179, and U.S. patent application Ser. No. 12/966,948 are also incorporated by reference herein.

Distal Catheter Exemplary Embodiments

With reference again to FIG. 1, the distal catheter 2030 is configured to be inserted through the arterial access device distal to the ICA and cerebral vessels, to a location as far as the thrombotic occlusion 10. The distal catheter 2030 has a length longer than the length of the arterial access device such that the distal catheter's distal end can protrude from the distal opening of the arterial access device by about 15-25 cm. The distal catheter is also more flexible than the arterial access device, due to the anatomy of the distal vasculature. A proximal port 2035 with a hemostasis valve may be situated on the proximal end of distal catheter 2030, to allow introduction of devices such as a microcatheter, guide wire, or thrombectomy device while preventing or minimizing blood loss during the procedure. In an embodiment, this valve is an adjustable-opening valve such as a Tuohy-Borst or rotating hemostasis valve (RHV). The hemostasis valve may be integral to the catheter proximal adaptor, or may be attached separately to the proximal end of the catheter via a Luer connection.

As with the arterial access device, the distal catheter 2030 may also be made with a two or more layer construction as described above. The distal catheter may be configured according to the description of the working portion of the arterial access device described above. In addition, the distal catheter may have a radiopaque marker at the distal tip to facilitate placement of the device using fluoroscopy. In an embodiment, the working portion of the device may have a hydrophilic coating to improve the ease of advancement of the device through the vasculature. In an embodiment, the distal-most portion is constructed to be more flexible than the proximal portion, by means as described above for the arterial access device.

The distal catheter 2030 has a working length configured to reach the terminal ICA and cerebral vessels when placed through the arterial access device 2010. In an embodiment, the working length is 40 to 80 cm. A distal catheter with this length would allow a much higher rate of aspiration than catheters designed for transfemoral access. For example, a distal catheter configured for transfemoral access to the cerebral circulation has a length of 115 cm and an inner diameter of 0.057" (the DAC 057 Catheter, Concentric Medical, Mountain View, Calif.) has a flow rate of 113 ml/min with fluid of 3.2 centipoise (cp, equivalent to blood) when connected to an aspiration pump set at a vacuum of 22 inHg. A distal catheter 2030 configured for transcervical access into the CCA to the cerebral circulation (such as described herein) may have a length of 50 cm, with a similar inner diameter. As flow resistance is linear with length of the tube according to Poiseuille's equation for flow through a tube, the catheter 2030 would have a flow rate of more than twice the transfemoral catheter, specifically a flow rate of 260 ml/min with 3.2 cp fluid when connected to an aspiration pump set at 22 inHg, or, about 2.3 times the aspiration rate of a transfemoral system. A similar increase in aspiration rate would also be seen with manual syringe aspiration or other aspiration source. In addition, because the transcervical access site is much closer than the transfemoral site with many less turns, there is less need for as high a degree of torque strength in the walls of the catheter, thus a transcervically placed catheter 2030 may be constructed with thinner wall construction, with equal or better ability to be placed in the target anatomy. A thinner wall would result in large inner lumen, yielding even more advantage in flow rate. As the flow resistance is proportional to diameter to the fourth power, even small improvements in luminal area result in larger advances in increased flow rate. In an embodiment, a distal catheter may be sized to reach the terminal ICA only (and not the more distal cerebral arteries). In this embodiment, the distal catheter may have an inner diameter of 0.070" to 0.095" and a length of 25-50 cm. In another embodiment, the distal catheter may be sized to reach the more distal cerebral arteries, with an inner diameter of 0.035" to 0.060" and a length of 40-80 cm.

As with the arterial access device, the distal catheter may have a variable stiffness shaft. In this embodiment, the distal-most portion (which may have a length of about 3 to about 6 cm) of the distal catheter may be configured to be more flexible to accommodate the curvature in the cerebral vessels. This additional flexibility may be achieved by using a lower durometer outer jacket material in this section. The shaft may have increasingly stiff sections towards the more proximal section of the shaft, with the proximal most portion having the stiffest shaft section.

In an embodiment, an occlusion balloon 2040 may be disposed on the distal catheter 2030 and can be used to occlude an artery such as to limit forward arterial flow or pressure, which would improve the conditions that permit aspiration as well as removal of the occlusion.

With reference still to FIG. 1, the distal catheter 2030 may also include a proximal adaptor with a Y-arm for a flow line 2045 (or shunt). The flow line 2045 has an internal lumen that communicates with an internal lumen of the distal catheter 2030. The proximal adaptor also includes a proximal hemostasis valve 2035 for the insertion of guidewires, microcatheters, or other catheters. In an embodiment, the proximal adaptor is permanently attached to the distal catheter 2030. In another embodiment, the proximal adaptor is a female Luer connector to which a separate Tuohy-Borst valve with a Y-arm can be attached.

Figure 6:
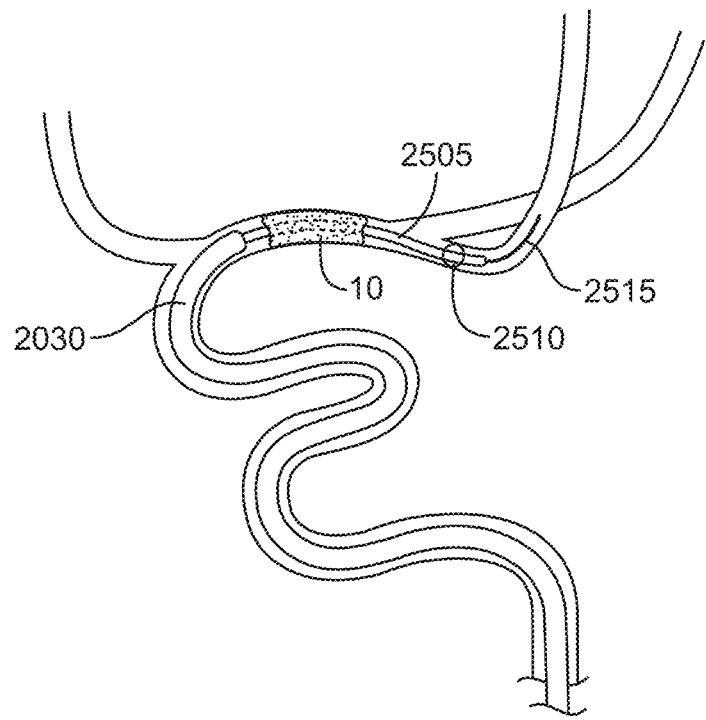
FIG. 6 illustrates an embodiment of a balloon-tipped anchor device.

In another embodiment, a distal catheter system includes an anchor device which is configured to be easily navigable through the vasculature to a location distal to the cerebral occlusion. When the anchor is deployed, it may be used as a rail and counter force to facilitate advancement of the distal catheter to the proximal face of the occlusion. An example as shown in FIG. 6 is a microcatheter 2505 with a distal balloon 2510. The microcatheter 2505 is placed over a guidewire 2515 through the occlusion 10 and then the distal balloon 2510 is inflated. Alternately, the microcatheter has an atraumatic guidewire tip built in and is advanced as a stand-alone device. The distal catheter 2030 can then use the shaft of the microcatheter 2505 as a rail to be advanced towards the occlusion 10, as is done in conventional techniques. However, because the balloon 2510 is inflated, the distal end of the microcatheter 2505 is anchored against the clot and/or the vessel wall and provides counter force to the advancing distal catheter 2030. Some of the force may be translated to the occlusion itself, and may help remove the clot. The guidewire 2515 remains in place during this maneuver, such that if the anchor (i.e., the balloon 2510) and distal catheter 2030 need to be re-advanced to attempt again to remove the occlusion 10, access is maintained across the occlusion with the guide wire 2515.

The atraumatic distal anchor can be a device other than a balloon. For example, other atraumatic distal anchors may include microcatheters with mechanically expandable-tips such as a braid, coil, or molly-bolt construction. The expandable tip can be configured to be sufficiently soft and to provide sufficient force along a length of the microcatheter so as to reduce focal pressure against the vessel wall and minimize vessel wall injury.

Figure 7:
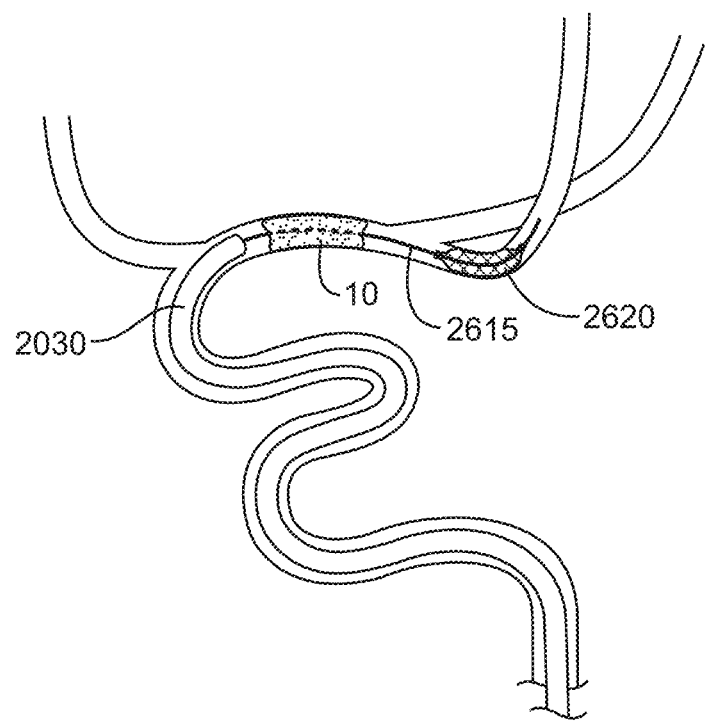
FIG. 7 illustrates an embodiment of a mechanically expandable-tipped anchor guide wire.

Another variation of this embodiment as shown in FIG. 7 is a guidewire 2615 with an expandable tip 2620 such as a balloon or expandable cage or stent. The guidewire 2615 may be placed in the vasculature using a microcatheter and then deployed when the microcatheter is retracted. The expandable portion of the guidewire 2615 device may be formed from separate braided filaments or cut from a single hypotube and expand with a counterforce actuating member. For example the proximal end of the expandable tip may be attached to the distal end of a hollow hypotube, and the distal end attached to a wire which runs the length of the hypotype. When the wire is pulled back, the expandable tip is shortened in length and expanded in diameter. Pushing the wire forward would collapse the expandable tip.

Figure 8:
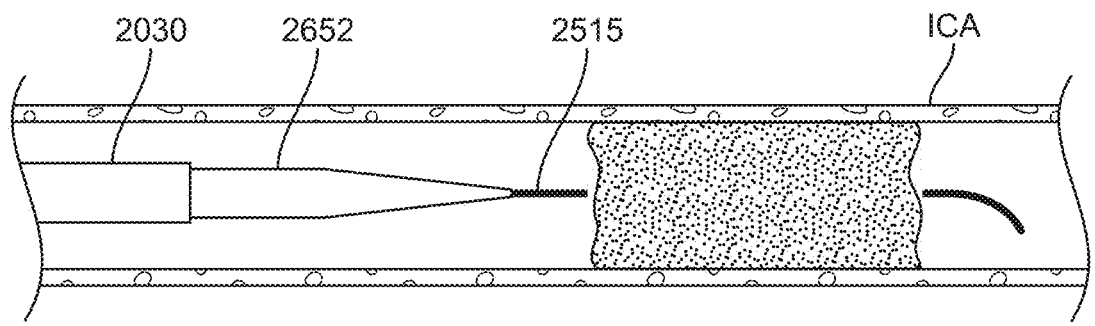
FIG. 8 illustrates an embodiment of a distal catheter with a tapered co-axial inner member.

A cause of difficulty in advancing larger size catheters is the mismatch between the catheter and the inner components. One technique for advancing the larger size catheters is called a tri-axial technique in which a smaller catheter, either a microcatheter or a smaller distal catheter, is placed between the large catheter and the guide wire. However, with current systems the smaller catheter has a diameter mismatch between either the larger catheter, the guide wire, or both, which creates a step in the system's leading edge as the system is advanced in the vasculature. This step may cause difficulty when navigating very curved vessels, especially at a location where there is a side-branch, for example the ophthalmic artery. In an embodiment, as shown in FIG. 8, the distal catheter 2030 is supplied with a tapered co-axial inner member 2652 that replaces the smaller catheter generally used. The inner member 2652 is sized and shaped to be inserted through the internal lumen of the distal catheter. The inner member 2652 has a tapered region with an outer diameter that forms a smooth transition between the inner diameter of the distal catheter 203 and the outer diameter of a guidewire 2515 or microcatheter that extends through an internal lumen of the inner member 2652. In an embodiment, the tapered dilator or inner member 2652, when positioned within the distal catheter, creates a smooth transition between the distal-most tip of the larger distal catheter 2030 and the outer diameter of a guide wire 2515 which may be in the range of 0.014" and 0.018" diameter for example. For example, the inner luminal diameter may be between 0.020" and 0.024". In another embodiment, the inner diameter is configured to accept a microcatheter with an outer diameter in the range of 0.030" to 0.040" or an 0.035" guide wire in the inner lumen, for example the inner luminal diameter may be 0.042" to 0.044".

Figure 9:
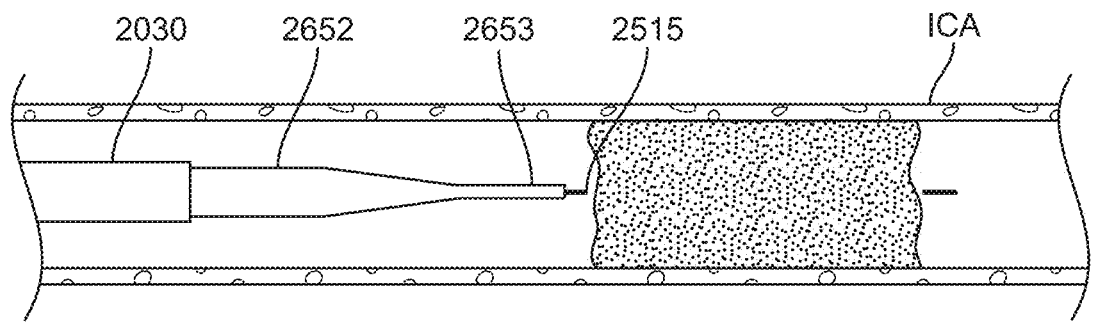
FIG. 9 illustrates another embodiment of a distal catheter with a tapered co-axial inner member.

In a variation of this embodiment, shown in FIG. 9, in addition to the tapered region, the inner member 2652 includes an extension formed of a uniform diameter or a single diameter, distal-most region 2653 that extends distally past the tapered portion of the inner member 2652. In this embodiment the distal region 2653 of the inner member 2652 may perform some or all of the functions that a microcatheter would do during a stroke interventional procedure, for example cross the occlusion to perform distal angiograms, inject intraarterial thrombolytic agents into the clot, or deliver mechanical thrombectomy devices such as coil retrievers or stent retrievers. In this manner, a microcatheter would not need to be exchanged for the dilator for these steps to occur.

The material of the dilator (inner member 2652) is flexible enough and the taper is long enough to create a smooth transition between the flexibility of the guide wire and the distal catheter. This configuration will facilitate advancement of the distal catheter through the curved anatomy and into the target cerebral vasculature. In an embodiment, the dilator is constructed to have variable stiffness, for example the distal most section is made from softer material, with increasingly harder materials towards the more proximal sections.

Figure 10:
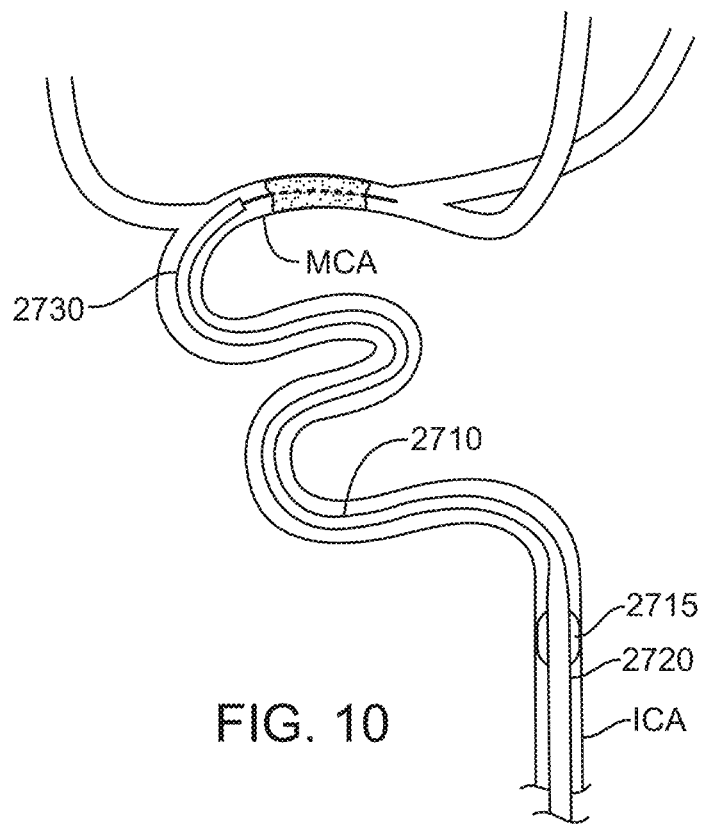
FIG. 10 illustrates an embodiment of a combined arterial access device and distal catheter.

In an embodiment, distal end of the tapered dilator has a radiopaque marker such as a platinum/iridium band, a tungsten, platinum, or tantalum-impregnated polymer, or other radiopaque marker. In an embodiment, the tapered dilator is constructed with variable stiffness. For example, the distal segment of the dilator may be constructed with a softer material, with successively stiffer materials towards the proximal end. As shown in FIG. 1, the distal catheter 2030 can be its own catheter that is separate and removable from the arterial access device. In another embodiment, shown in FIG. 10, the distal catheter and the arterial access device are combined to be a single device 2710 with a continuous lumen extending through the length of the device. A proximal portion 2720 comprises the arterial access sheath and a distal portion 2730 functions as the distal catheter. An occlusion balloon 2715 is located between the distal and proximal portion. The distal portion 2730 is constructed to be more suited for navigating the cerebral vasculature. In particular, the distal portion 2730 is more flexible and tapered to a smaller diameter than the proximal portion 2720.

Figure 11:
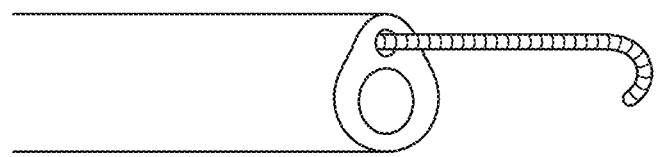
FIGS. 11 and 12 illustrate embodiments of distal catheters having second lumens to maintain guide wire access.
Figure 12:
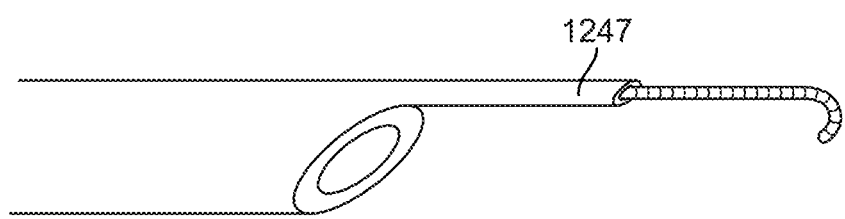

In another embodiment, as shown in FIGS. 11 and 12, the distal catheter has a second lumen to maintain guide wire access to facilitate re-advancement or exchange of the distal catheter without recrossing the target anatomy. In an embodiment, shown in FIG. 11, the distal catheter has two lumens which terminate together at the distal tip: a main lumen and a second guidewire lumen. The termination may be such that a distal-facing surface is arranged at an angle (relative to the longitudinal axis of the catheter), to facilitate tracking of the catheter through the vasculature. In another embodiment, shown in FIG. 12, the second guidewire lumen is inside an extension 1247 that extends out past the termination of the main lumen. The extension 1247 is a distal-most region of the distal catheter that protrudes distally past an opening formed by the main lumen. The extension 1247 forms a shaft having a reduced outer diameter relative to the outer diameter of the distal catheter around the main lumen. The second lumen is smaller than the shaft of the main distal catheter, and may be positioned in or across an occlusion while the distal end of the main lumen is positioned on the proximal face of an occlusion. The distal end of the main lumen may be terminated at an angle as well, to facilitate tracking of the device.

In yet another embodiment, the distal catheter has an expandable tip portion. The expandable tip facilitates aspiration of an occlusion when an aspiration device is connected to the proximal portion of the distal catheter. The expandable tip portion may be constructed with a mechanical structure such as a braid or stent structure, which can open or close in a repeatable manner. The mechanism for opening the tip may be a pull-wire which shortens the expandable portion, or an outer retention sleeve which maintains the distal section in a small diameter but when retracted allows the distal tip to expand. The distal section may be covered with a membrane such that when aspiration is applied, either with the tip expanded or not, a vacuum may be applied at the very tip of the catheter. The expandable tip allows the catheter to maintain a small profile during tracking of the catheter to the target anatomy, but then expands the distal luminal area for facilitated capture of occlusive material such as thrombus. The thrombus, once captured into the distal catheter, may be sucked all the way into the aspiration device, or alternately will be lodged in the lumen of the distal catheter where the catheter is no longer expanded, and at that point can be removed by retraction of the entire distal catheter.

Figure 13:
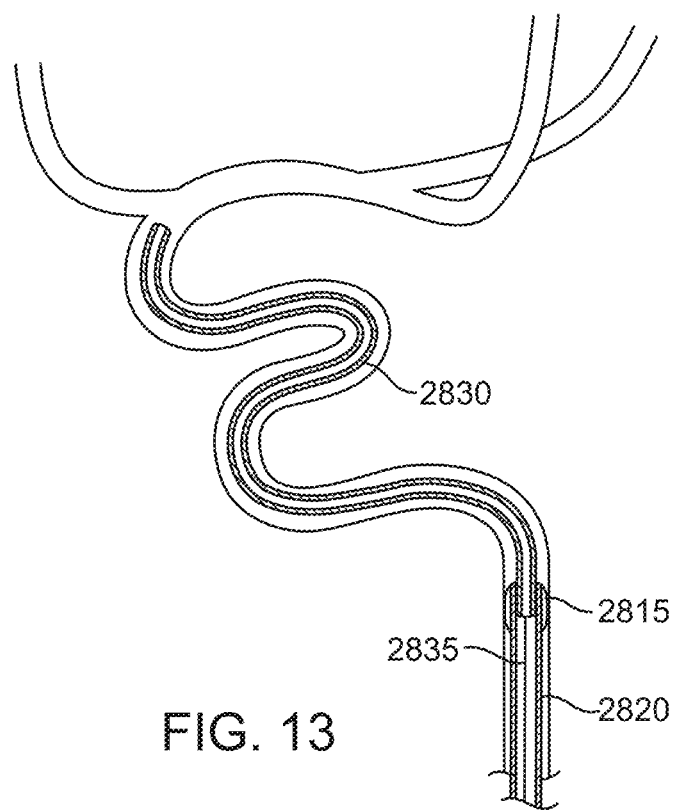
FIG. 13 illustrates an embodiment of a distal catheter and arterial access device configured to be telescoping.

In another embodiment, shown in FIG. 13, the distal catheter 2830 is a telescopic attachment to the distal portion of the arterial access device 2820. The distal region of the arterial access device 2820 has one or more structures that telescopically extend in the distal direction along the longitudinal axis of the arterial access device. The structures may also be telescopically collapsed such that they do not extend past the distal end of the arterial access device. When the structures are telescopically expanded past the distal end of the arterial access device, the structures collectively form a continuous inner lumen. A tether element such as a wire 2835 may be connected to the distal portion 2830 and extends out the proximal end of arterial access device such that the telescoping actuation may be accomplished from the proximal end of the arterial access device. An expandable member, such as balloon 2815, may be positioned on the device 2820.

Figure 14:
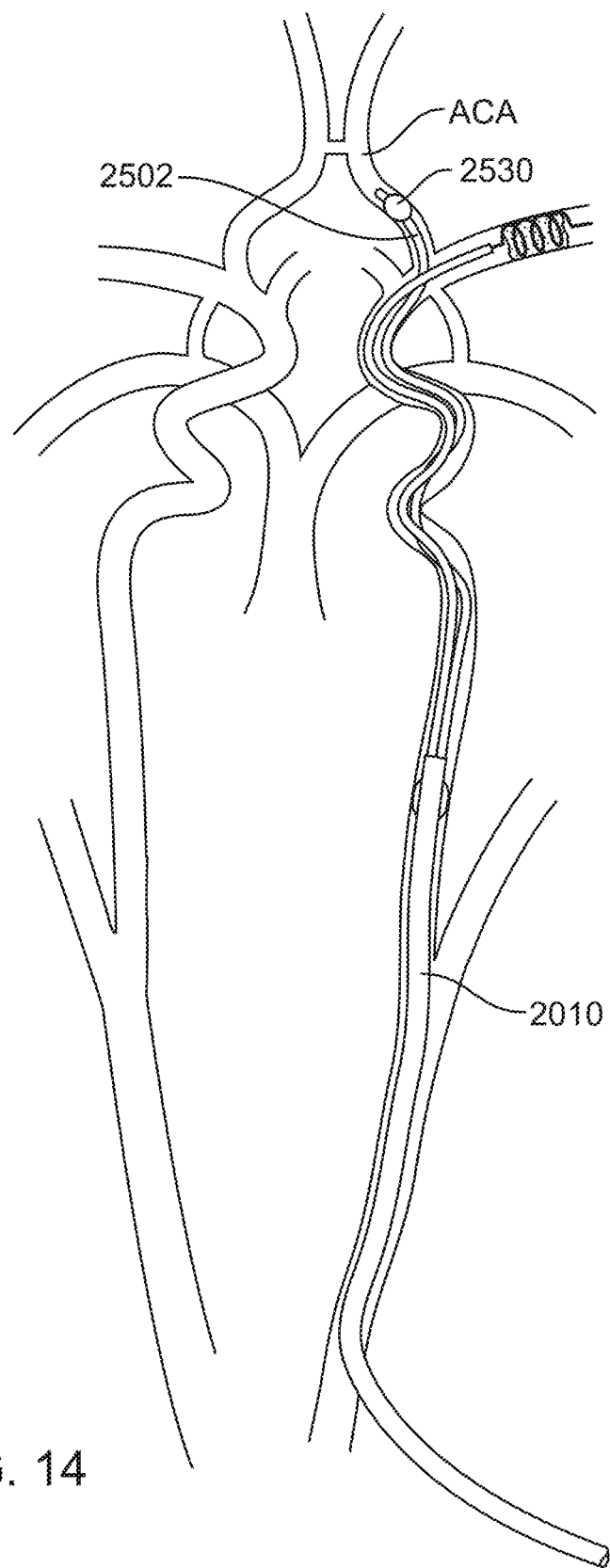
FIG. 14 illustrates an alternate embodiment of the system with the addition of an occlusion device.

FIG. 14 shows an alternate embodiment of the system wherein a secondary device, such as a balloon catheter 2502, is advanced through the arterial access device 2010 and into a collateral cerebral artery such as the anterior cerebral artery ACA. The balloon catheter 2502 includes an expandable balloon 2530 that can be expanded in the collateral cerebral artery to occlude that artery. Occlusion of the collateral cerebral artery enhances suction and reverse flow through the cerebral vasculature, as described in detail below.

Exemplary Embodiments of Aspiration and Flow Control

Either or both the arterial access device 2010 and the distal catheter 2030 may be connected to sources of passive or active aspiration via flow lines 2025 or 2045 (FIG. 1) on the devices. The mode of aspiration may be different for each device.

Figure 15:
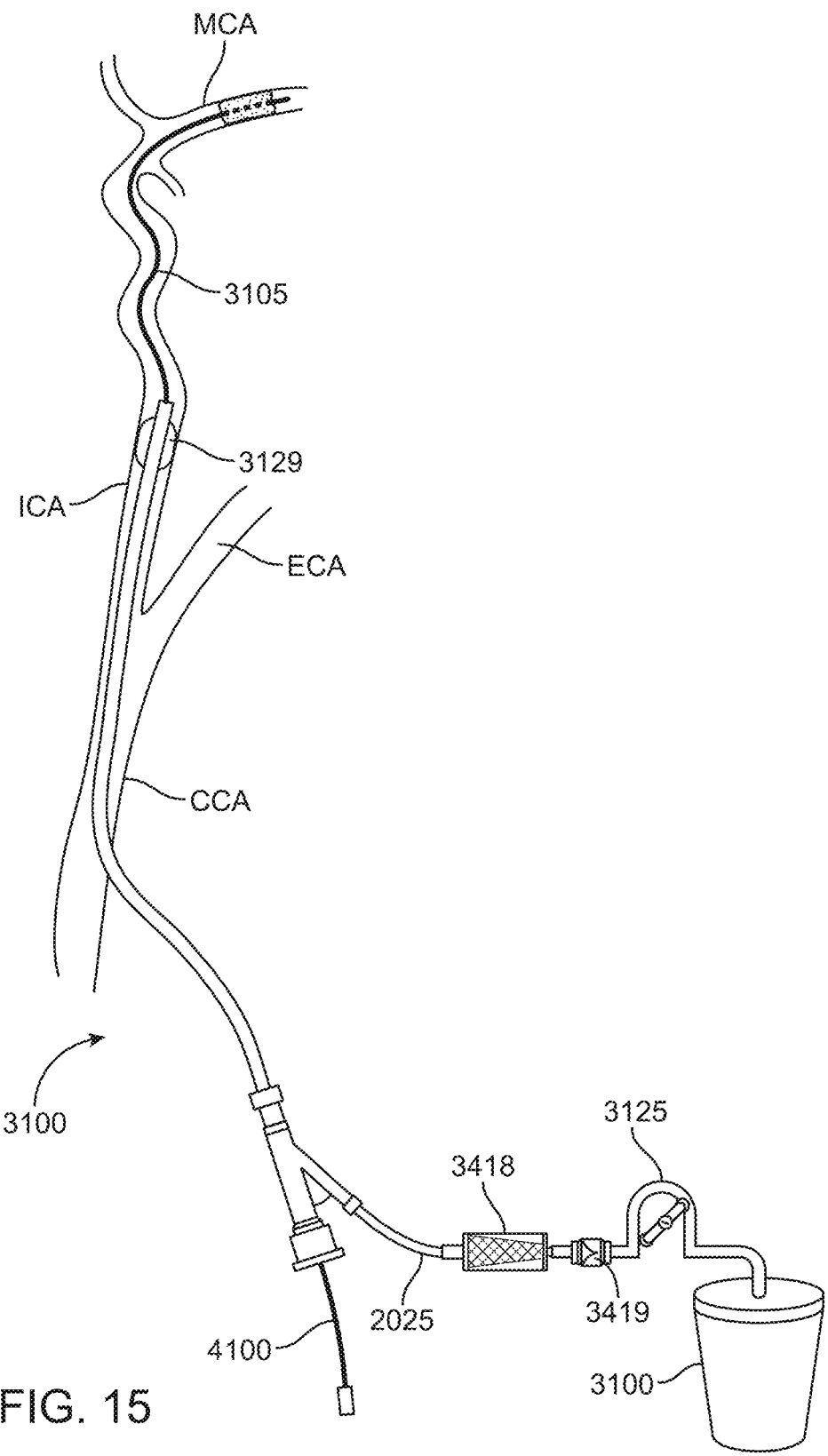
FIG. 15 illustrates an embodiment of the system with the addition of an aspiration source, filter and one-way check valve attached to the arterial access device.
Figure 16:
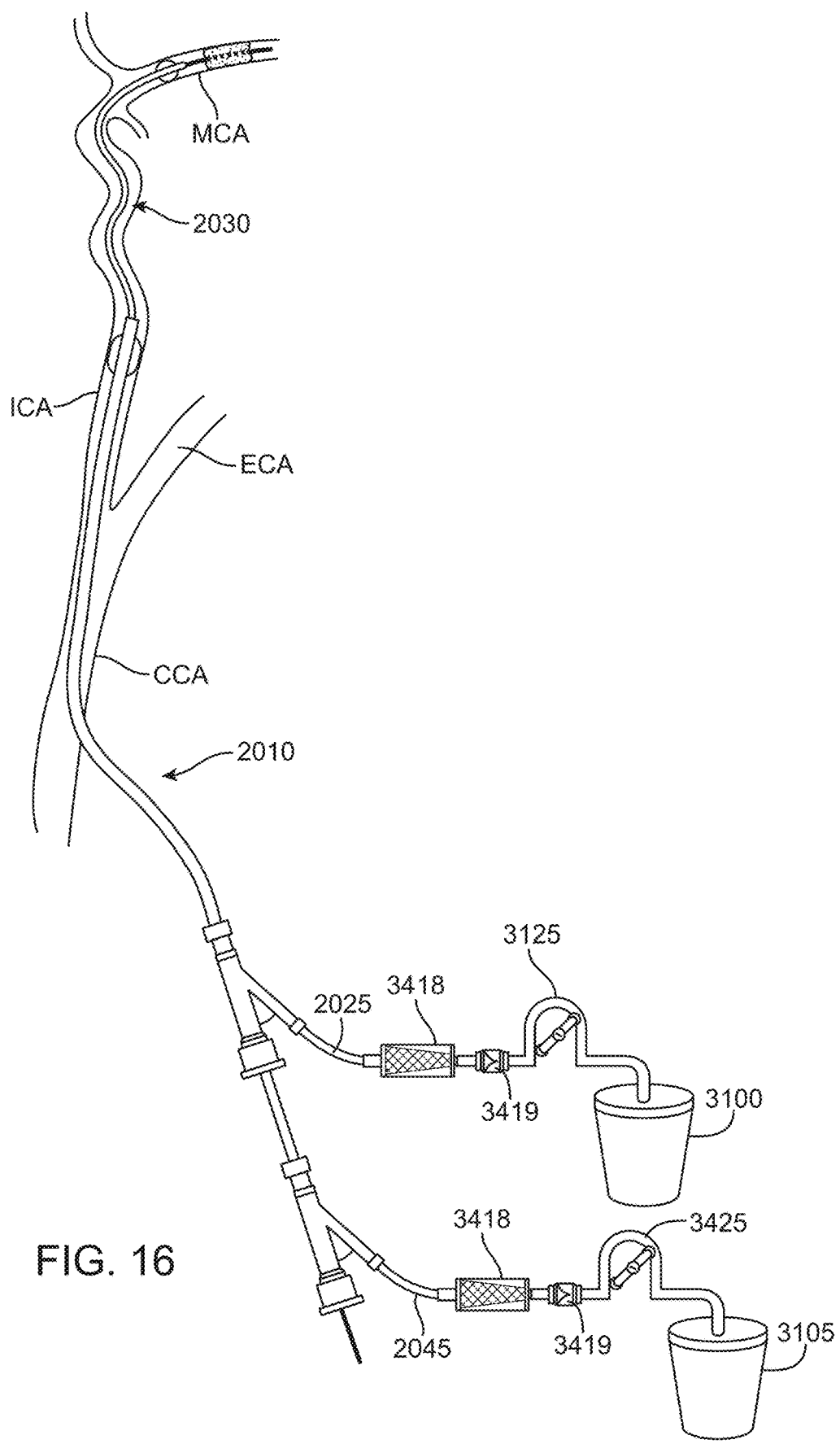
FIG. 16 illustrates an embodiment of the system with the addition of an aspiration source, filter and one-way check valve attached to both the arterial access device and distal catheter.

In FIG. 15, the flow line 2025 of the arterial access device 2010 is connected to a delivery location, such as a receptacle 3100. A source of aspiration 3125 may be coupled to the flow line 2025. The receptacle 3100 and source of aspiration 3125 may be separate or may be combined into a single device such as a syringe. A filter 3418 and/or a check valve 3419 may be coupled with flow line 2025. In FIG. 16, the flow line 2045 of the distal catheter 2030 is additionally or alternately connected to a separate aspiration source 3425 and delivery location, such as receptacle 3105. The aspiration source 3425 and delivery location may be combined into a single device such as a syringe. A filter 3418 and/or a check valve 3419 may coupled with the flow line 2045.

Figure 17:
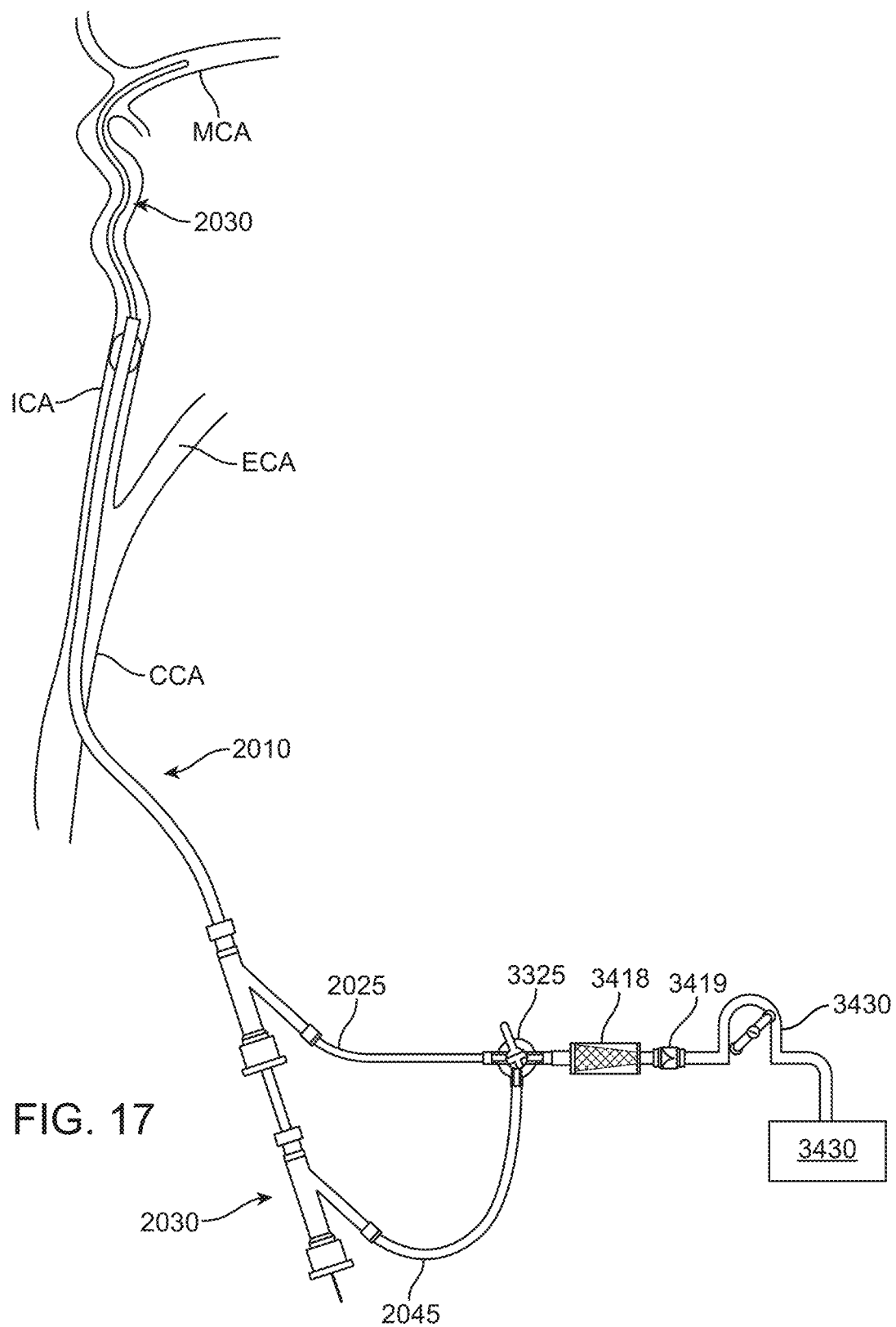
FIG. 17 illustrates an embodiment of the system with the addition of a single aspiration source, filter and one-way check valve attached to both the arterial access device and distal catheter, and a valve connecting the two devices to the aspiration source.

FIG. 17 shows a system whereby both the arterial access device 2010 and distal catheter 2030 are connected to the same aspiration source 3430 via flow lines 2025 and 2045, respectively. A valve 3325 controls which device is connected to the aspiration source 3430. The valve may enable one device, the other device, both devices, or neither device to be connected to the aspiration source at any given time. The valve may be a 3-way or 4-way stopcock. Alternately, the valve may be a flow controller with a simple actuation which selects the configuration as described above.

Figure 18:
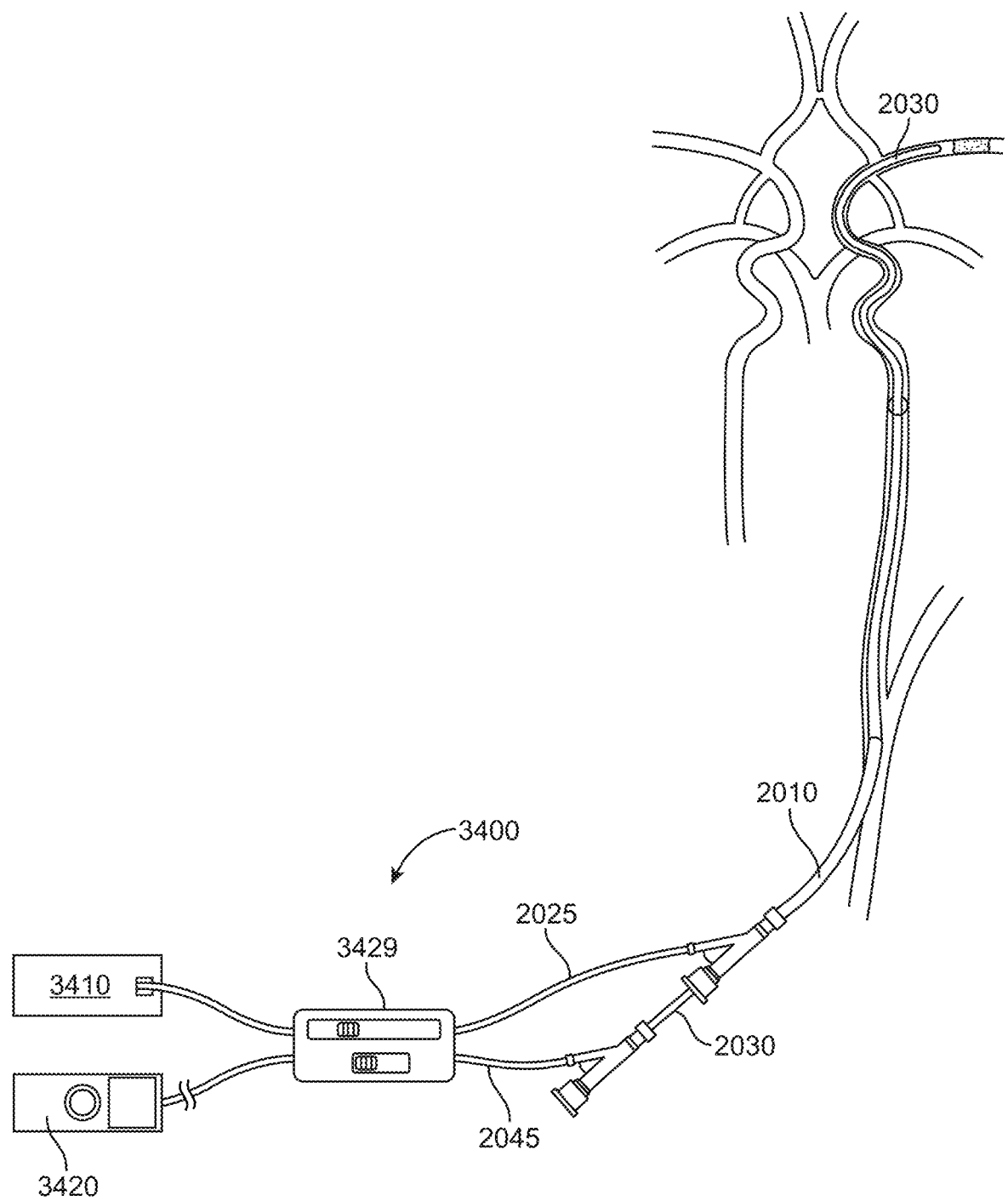
FIG. 18 illustrates an embodiment of the system with the addition of a flow controller attached to both the arterial access device and distal catheter.

In an embodiment, a flow controller may facilitate control of multiple means of aspiration through multiple devices in a single unit. This configuration may facilitate use of the system by a single operator. The flow controller may include one or more control interfaces that a user may actuate to regulate which device is being aspirated, for example the arterial access device, the distal catheter, both, or neither. FIG. 18 shows an embodiment of a system that utilizes such a flow controller 3400. The flow controller 3400 is connected to the flow line 2025 of the arterial access device 2010 as well as to the flow line 2045 of the distal catheter 2030. In this manner, the flow lines 2025 and 2045 permit fluid to flow from the arterial access device 2010 and the catheter 2030, respectively, to the flow controller 3400. The controller 3400 may be connected to either or both a passive source of aspiration 3410 and an active source of aspiration 3420. The flow controller housing 3429 contains control mechanisms to determine how and when each device is connected to each source of aspiration. The control mechanisms may also control the level of aspiration from each source. In addition, the controller may include a control that permits a pulsatile aspiration mode which may facilitate the breaking up and aspiration of the cerebral occlusion. The flow controller may have an interface for switching between continuous and pulsatile aspiration modes. The control mechanisms may be designed to be operable using one hand. For example, the control mechanisms may be toggle switches, push button switches, slider buttons, or the like. In an embodiment, the flow controller 3400 has an interface that can enable the user to restore immediate antegrade flow to the cerebral circulation, for example with a single button or switch that simultaneously deflates the occlusion balloon on the arterial access device and stops aspiration.

The active source of aspiration may be an aspiration pump, a regular or locking syringe, a hand-held aspirator, hospital suction, or the like. In one embodiment, a locking syringe (for example a VacLok Syringe) is attached to the flow controller and the plunger is pulled back into a locked position by the user while the connection to the flow line is closed prior to the thrombectomy step of the procedure. During the procedure when the tip of the aspiration device (either the arterial access device or the distal catheter) is near or at the face of the occlusion, the user may open the connection to the aspiration syringe. This would enable the maximum level of aspiration in a rapid fashion with one user, something that is currently not possible with existing technologies. In another embodiment, the aspiration source is a hand-held aspirator which is configured to be able to aspirate and refill without disconnecting the aspiration device. In an example of this embodiment, the hand-held aspirator contains a chamber with a plunger that is moved up and down with a single-handed actuator. The chamber includes input and output valves, such that when the plunger is moved up and down there is a continuous source of aspiration into and out of the chamber without the need to remove and empty the chamber as would be needed with a syringe. The chamber input is connected to the catheter, and the chamber output is connected to a collection receptacle such as blood-collection bag. In an embodiment, this aspiration source is configured to be used with one hand only.

One disadvantage of current sources of aspiration is that the aspirated blood is received into an external reservoir or syringe. This blood is generally discarded at the end of the procedure, and as such represents blood loss from the patient. In addition, pumps such as centrifugal or peristaltic pumps are known to cause damage to blood cells. Although it is possible to return blood from the external reservoir to the patient, the blood has been exposed to air or has been static for a period of time, and there is risk of thrombus formation or damage to the blood cells. Usually, aspirated blood is not returned to the patient to avoid risk of thromboembolism.

Figure 19:
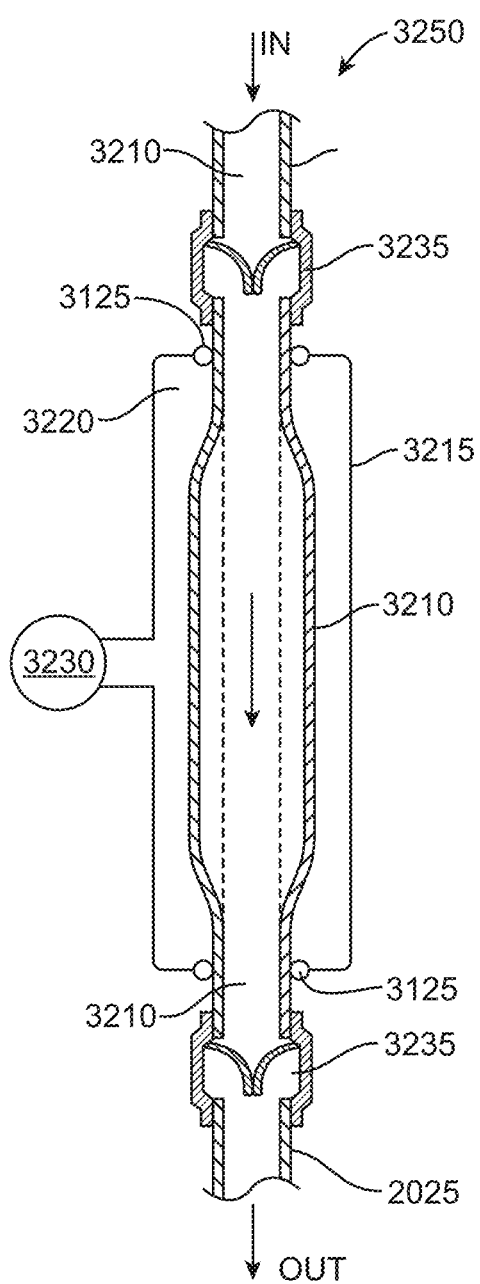
FIG. 19 illustrates an embodiment of an aspiration source.

FIG. 19 shows a cross-sectional view of an exemplary aspiration pump device 3250 which is configured not to harm blood cells and which may be configured to return blood to the central venous system in real time during the procedure, so there is no reservoir in which the blood remains static. The pump 3250 may be connected to either or both the arterial access device 2010 and distal catheter 2030. The pump device 3250 includes a housing 3215 that encloses a chamber 3220 in which is contained a portion of the flow line 2025. An expandable portion 3210 of the flow line 2025 contained within the chamber 3220 is formed of an elastic material that is at a reduced diameter in its natural state (shown in phantom lines in FIG. 19) but may be configured to change to an expanded diameter (shown in solid lines in FIG. 19). One or more seals 3125, such as O-rings, seal the interface between the chamber 3220 and the flow line 2025. A vacuum source 3230 is coupled to the chamber 3220 and is configured to be operated to vary the pressure within the chamber 3220. Two one-way check valves 3235 are located in the flow line 2025 on either side of the expandable portion 3210.

In operation of the pump device 3250, the vacuum source 3230 is operated to create a reduced pressure within the chamber 3220 relative to the pressure within the flow line lumen 3210. The pressure differential between the chamber 3220 and the flow line lumen 3210 causes the expandable portion 3210 of the flow line 2025 to expand to an increased volume within the chamber 3220, as shown in solid lines in FIG. 32. This expansion causes blood to be pulled into the expandable portion 3210 from the sheath side of the flow line, shown by the "in" arrow, as controlled by the check valves 3235. The vacuum source 3230 may then be turned off so as to normalize the pressure within the chamber 3220. This causes the expandable portion 3210 to revert to its smaller, natural diameter, as shown in phantom lines in FIG. 19. The check valves 3235 causes the blood within the previously-expanded region of the flow line 2025 to be expelled towards location 3120, as shown by the "out" arrow in FIG. 19. The vacuum source 3230 may be operated so as to oscillate the expandable portion 3210 between the expanded and retracted state and together with the one-way check valves 3235 thereby drive fluid through the flow line lumen 3210.

Figure 20:
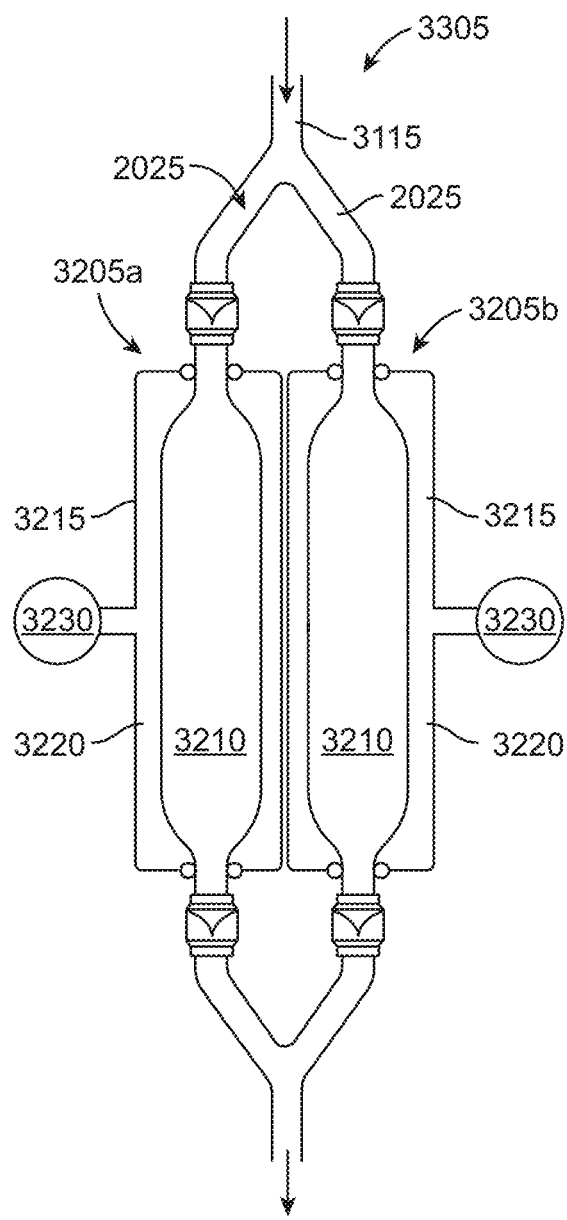
FIG. 20 illustrates an alternate embodiment of an aspiration source.
Figure 32:
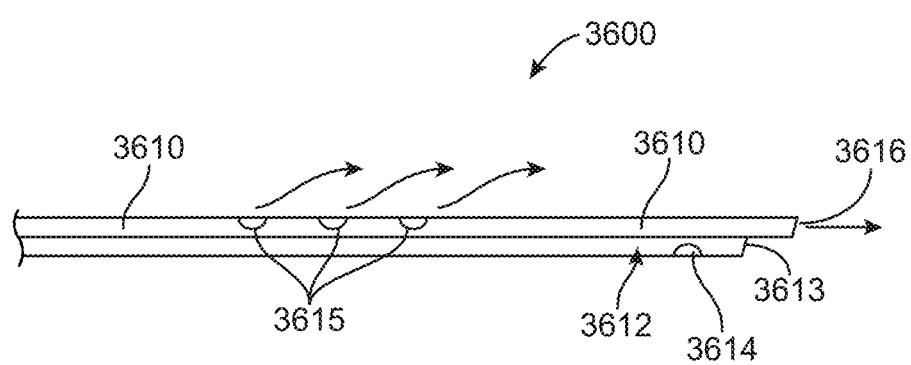
FIG. 32 illustrates an alternate embodiment of a distal perfusion catheter.

FIG. 20 shows a pump system 3305 that includes a pair of pump device 3205a and 3205b, each of which is of the type shown in FIG. 32. That is, each device 3205 includes a housing 3215 that contains a chamber in which a portion of the flow line 2025 is contained. The pump devices 3205a and 3205b are connected in parallel to the flow line 2025 such that each pump device 3205 has a flow line 2025 with an expandable portion 3210. The pair of pump devices 3205a and 3205b may be alternated between expanded and retracted states to create a relatively continuous flow state through the pump system 3305. For example, the pump device 3205a may be in the expanded state while the pump 3205b may be in the retracted state such that the pumps 3205a and 3205b are collectively driving fluid through the pump system 3305 without interruption.

A further advantage pump system 3250 or 3305 is that it may be used in conjunction with a passive reverse flow system which is configured to return blood to the central venous system, as is disclosed elsewhere in this document. These two systems may share a venous return line, and are connected by a valve or other flow control device.

Figure 21:
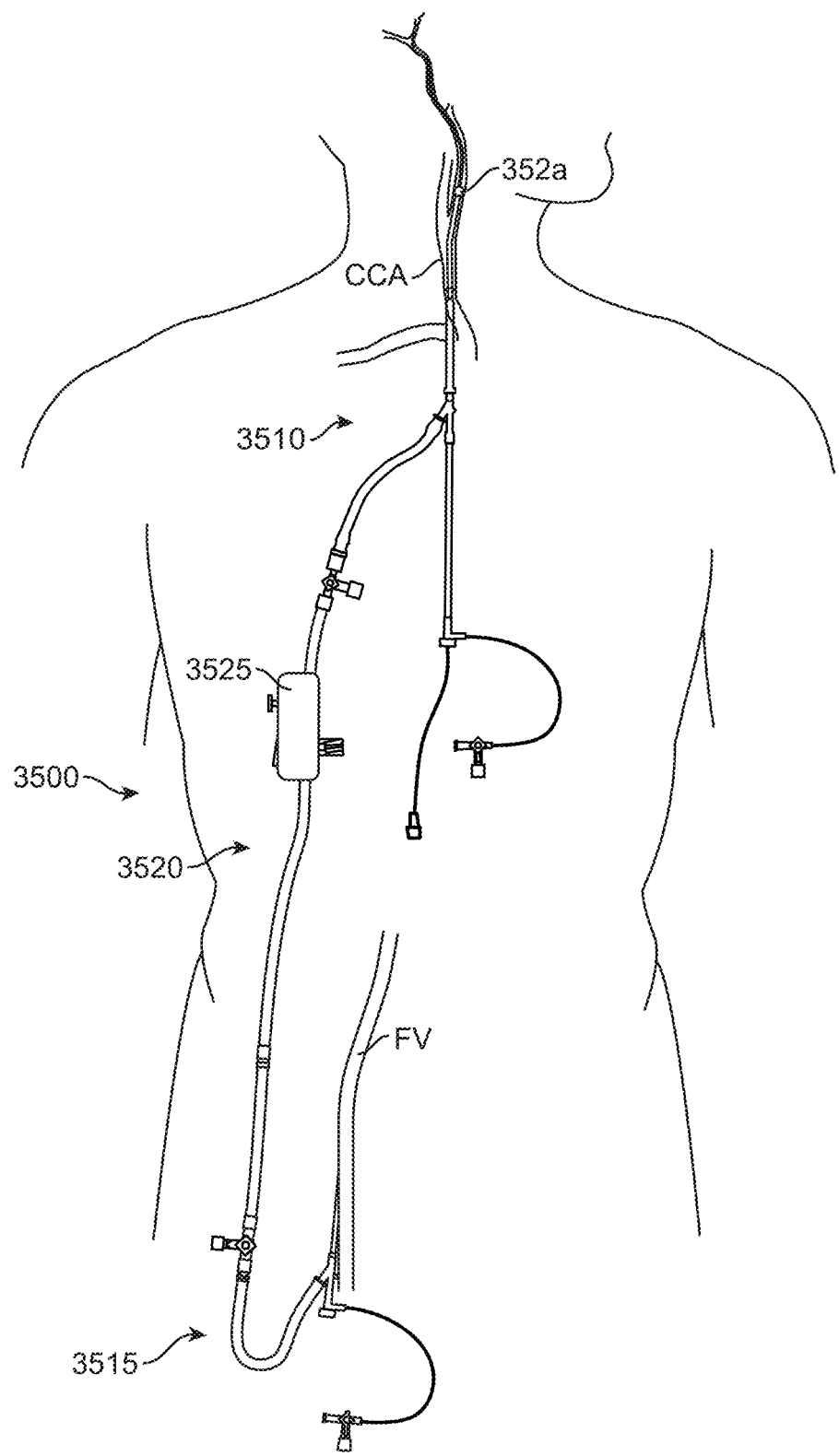
FIG. 21 illustrates an embodiment of the system with the addition of a flow reverse circuit that includes a venous return site.

The passive source of aspiration may be a site with lower pressure, for example a sheath inserted into a central vein (for venous return) or an IV bag placed at a vertical level that would vary depending on what amount of negative pressure is desired. FIG. 21 shows an exemplary embodiment of a system 3500 that uses venous return to establish passive retrograde flow into the arterial access device. The system 3500 includes the arterial access device 3510, a venous return device 3515, and a flow line 3520 that provides a passageway for retrograde flow from the arterial access device 3510 to the venous return device 3515. A flow control assembly 3525 interacts with the flow line 3520. The flow control assembly 3525 is adapted to regulate and/or monitor the retrograde flow through the flow line 3520. The flow control assembly 3525 interacts with the flow pathway through the flow line 3520 to determine the state and level of flow through the flow line.

In an embodiment, the arterial access device 3510 at least partially inserts into the common carotid artery CCA and the venous return device 3515 at least partially inserts into a venous return site, such as the femoral vein or internal jugular vein, as described in more detail below. The venous return device 3515 can be inserted into the femoral vein FV via a percutaneous puncture in the groin. The arterial access device 3510 and the venous return device 3515 couple to opposite ends of the flow line 3520 at connectors. The distal end of the arterial access device 3510 with the occlusion element 3529 may be positioned in the ICA. Alternately, in some circumstances where the ICA access is extremely tortuous, it may be preferable to position the occlusion element more proximally in the common carotid artery. When flow through the internal carotid artery is blocked (using the occlusion element 3529), the natural pressure gradient between the internal carotid artery and the venous system causes blood to flow in a retrograde or reverse direction from the cerebral vasculature through the internal carotid artery and through the flow line 3520 into the venous system.

In another embodiment, the arterial access device 3510 accesses the common carotid artery CCA via a transcervical approach while the venous return device 3515 access a venous return site other than the femoral vein, such as the internal jugular vein. In another embodiment, the system provides retrograde flow from the carotid artery to an external receptacle, for example an IV bag, rather than to a venous return site. The arterial access device 3510 connects to the receptacle via the flow line 3520, which communicates with the flow control assembly 3525. The retrograde flow of blood is collected in the receptacle. If desired, the blood could be filtered and subsequently returned to the patient. The pressure of the receptacle could be set at zero pressure (atmospheric pressure) or even lower, causing the blood to flow in a reverse direction from the cerebral vasculature to the receptacle.

Exemplary Embodiments of Thrombectomy Devices

An exemplary embodiment of a thrombectomy device for use with any of the disclosed systems of devices is a device such as those described above but that are configured for transcervical placement. Specifically, the thrombectomy device has a working length which would allow it to extend out of the arterial access device 2010 or distal catheter 2030 with enough length to access and cross the cerebral occlusion. More specifically, a thrombectomy device with a working length of between 80 and 120 cm.

In an embodiment, a microcatheter which has been configured for transcervical access is included as part of system 100. More specifically, a microcatheter with a working length of between 100 and 140 cm is included in system 100. The microcatheter may be used for angiograms and/or delivery of thrombectomy devices.

Figure 22:
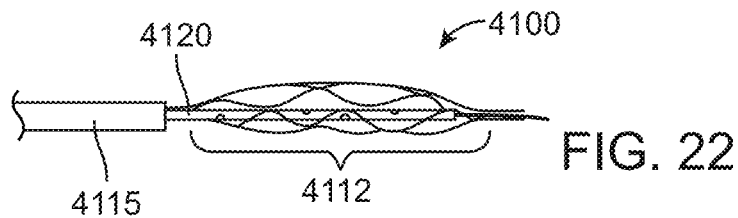
FIGS. 22-29 illustrate embodiments of thrombectomy devices.

Additional embodiments of thrombectomy devices are now described. FIG. 22 shows an enlarged, side view of a distal region of an exemplary thrombectomy device 4100 that is formed of a self-expandable member 4112 attached to an elongate flexible catheter 4115 that extends proximally from the expandable member 4112. The expandable member 4112 is formed of a plurality of longitudinal, intertwined or undulating struts that are arranged to form a plurality of cell structures that may be diamond-shaped. In an embodiment, the struts are coupled to a source of energy that permits sonic energy to be applied to the struts. The expandable member 4112 is configured to transition between a reduced size and an enlarged size wherein the expandable member 4112 expands radially outward from a first diameter to a second, greater diameter relative to the longitudinal axis of the catheter 4115. The expandable member 4112 may be formed for example from a single tube which has been laser cut in a geometry to create the struts, in a similar manner that many intravascular stents are manufactured. In an embodiment, the expandable member 4112 is made of shape memory material, such as Nitinol. The expandable member 4112 may be configured according to expandable members described in U.S. Patent Publication No. 20110009875, which is incorporated herein by reference in its entirety.

In use, the expandable member 4112 is advanced through the vascular anatomy via the arterial access device described above. The expandable member 4112 is positioned at the site of the thrombus while in the unexpanded state. The expandable member is then positioned within the location of the thrombus and caused to transition to its expanded state. In an embodiment, once the expandable member 4112 is expanded at the location of the thrombus, the expandable member is maintained in that location for a period of time in order to create a perfusion channel through the thrombus that causes the thrombus to be lysed by the resultant blood flow passing through the thrombus. In such an embodiment, it is possible but not necessary that the expandable member 4112 capture a portion of the thrombus for retrieval outside the patient. When a sufficient portion of the thrombus has been lysed to create a desired flow channel through the obstruction, or outright removal of the obstruction is achieved by the resultant blood flow, the expandable member 4112 may be withdrawn into the sheath 4100 and subsequently removed from the patient. The expandable portion may capture some or all of the thrombus while being withdrawn into the sheath.

In an embodiment, also shown in FIG. 22, an elongated perfusion catheter 4120 is positioned longitudinally through the expandable member 4112. The perfusion catheter 4120 has a plurality of perfusion holes that communicate with an internal lumen and a source of perfusion fluid. The perfusion catheter 4120 is configured to perfuse fluid outwardly through perfusion holes 4125. The perfusion holes may be used to perfuse thrombolytic agents such as urokinase or tPA to aid in the dissolution of the clot. Alternately, the perfusion holes may be used to perfuse neuroprotective agents and/or oxygenated blood.

Figure 23:

FIG. 23 shows another embodiment wherein an elongated mechanical member 4205 is positioned longitudinally through the expandable member 4112. The mechanical member 4205 generally extends along the longitudinal axis of the expandable member 4112. The mechanical member is configured to exert mechanical energy onto the thrombus when the expandable member 4112 is positioned within the thrombus. The mechanical member 4205 may be any of a variety of mechanical members, such as a corkscrew wire or a brush. The mechanical member can be moved to exert the mechanical energy, such as by rotating or vibrating the mechanical member 4205. The embodiments of FIGS. 16 and 17 may be combined to provide perfusion and aspiration capabilities along with mechanical disruption capabilities.

Figure 24:
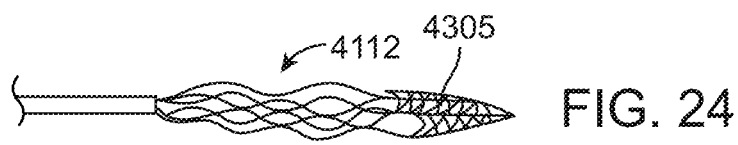
Figure 25:
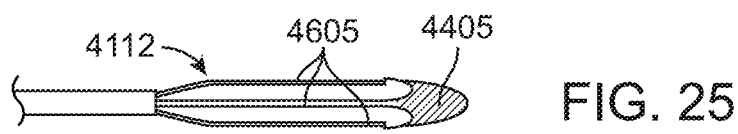

Various other features may be used with or coupled to the expandable member 4112. FIG. 24 shows an embodiment wherein a distal filter 4305 is positioned at or near the distal end of the expandable member 4112. The filter 4305 is configured to capture emboli which may be generated during removal of the thrombotic obstruction, either through natural lysis of the thrombus or mechanical retrieval of the thrombus. In the embodiment of FIG. 25, a parachute-shaped member 4405 is positioned at or near the distal end of the expandable member 4112. The embodiment of FIG. 19 includes a plurality of longitudinal struts 4605 that extend from a proximal end toward a distal end of the expandable member 4112, and are attached to parachute-shaped member 4405. The struts 4605 are configured to be pressed through the thrombus when deployed within the thrombus. When pressed through the thrombus, the struts 4605 pull the parachute-shaped member 4405 around the thrombus to capture it, and the device 4100 can then be withdrawn to pull the thrombus out of the artery.

Figure 26:

In the embodiment of FIG. 26 an expandable dilatation member 4505, for example a dilatation balloon is positioned within the expandable member 4112. The dilation member 4505 may be expanded to dilate the thrombotic occlusion and press the expandable member 4112. Once the dilation member is deflated, the expandable member which is now engaged with the clot may be pulled back to remove the thrombus out of the artery.

Figure 27:
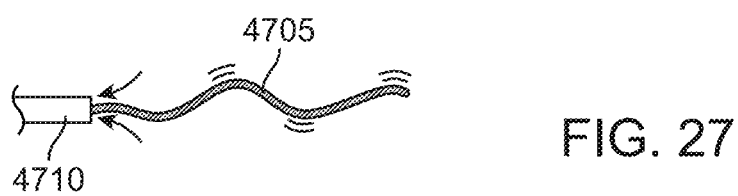

FIG. 27 shows another embodiment of a thrombectomy device comprised of an elongated element 4705 positioned at a distal end of a distal catheter 4710. The elongated element 4705 has an irregular shape along its longitudinal axis, such as a corkscrew or undulating shape. Alternately, the elongated element is slidably positioned inside distal catheter 4710. The elongated element 4705 may be made from spring material such as stainless steel or Nitinol, so that it may be retracted into distal catheter 4710 when crossing the clot. After crossing, the catheter 4710 is pulled back to expose the elongated element 4705 and allow it to take its irregular shape. The elongated element may be positioned at the site of the thrombus and then manipulated, such as by shaking, rotating, waving, spinning, or moving back and forth, so as to exert mechanical energy onto the thrombus to break up the thrombus. The distal catheter 4710 is connected to an aspiration source to aspirate the thrombus as it is being mechanically disrupted by elongated element 4705.

Figure 28:
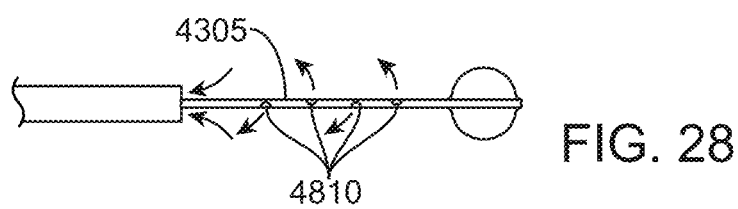

In the embodiment of FIG. 28, an elongated catheter 4805 is sized and shaped to be positioned within the thrombus. The catheter 4805 includes perfusion holes 4810 that can be used to spray a perfusion fluid onto the thrombus with sufficient force onto the thrombus to disrupt the thrombus. The elongated catheter 4805 may be delivered through another distal catheter 4820. The distal catheter 4820 may be connected to an aspiration source to aspirate the thrombus as it is being fluidly disrupted by the perfusion fluid from elongated catheter 4805. The distal end of the catheter 4805 may include an expandable occlusion element 4815 to prevent perfusion fluid or disrupted thrombus from traveling downstream.

Figure 29:
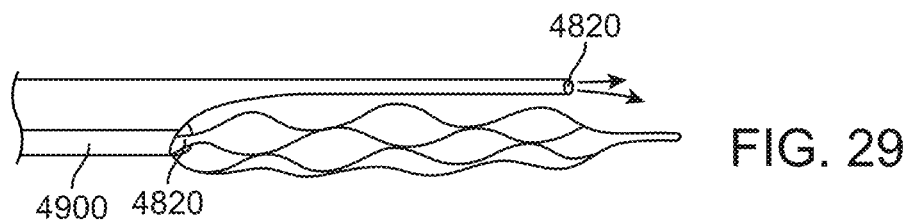

In another embodiment, shown in FIG. 29, a catheter 4900 includes dual lumens that run in parallel along the length of the catheter 4900. The dual lumens include an access lumen 4920 for deployment of an intervention device such as a thrombectomy device or a stentriever, as well as a perfusion lumen 4930 for transmission of perfusion fluid, thrombolytic agent, or for aspiration of thrombus material.

It should be appreciated that other mechanical thrombectomy catheters may be used in a similar manner with the vascular access and reverse flow system as described above. Mechanical thrombectomy devices may include variations on the thrombus retrieval device described earlier, such as coil-tipped retrievers, stent retrievers, expandable cages, wire or filament loops, graspers, brushes, or the like. These clot retrievers may include aspiration lumens to lower the risk of embolic debris leading to ischemic complications. Alternately, thrombectomy devices may include clot disruption elements such as fluid vortices, ultrasound or laser energy elements, balloons, or the like, coupled with flushing and aspiration to remove the thrombus. Some exemplary devices and methods are described in the following U.S. patents and patent Publications, which are all incorporated by reference in their entirety: U.S. Pat. Nos. 6,663,650, 6,730,104; 6,428,531, 6,379,325, 6,481,439, 6,929,632, 5,938,645, 6,824,545, 6,679,893, 6,685,722, 6,436,087, 5,794,629, U.S. Patent Pub. No. 20080177245, U.S. Patent Pub. No. 20090299393, U.S. Patent Pub. No. 20040133232, U.S. Patent Pub. No. 20020183783, U.S. Patent Pub. No. 20070198028, U.S. Patent Pub. No. 20060058836, U.S. Patent Pub. No. 20060058837, U.S. Patent Pub. No. 20060058838, U.S. Patent Pub. No. 20060058838, U.S. Patent Pub. No. 20030212384, and U.S. Patent Pub. No. 20020133111.

Figure 30:
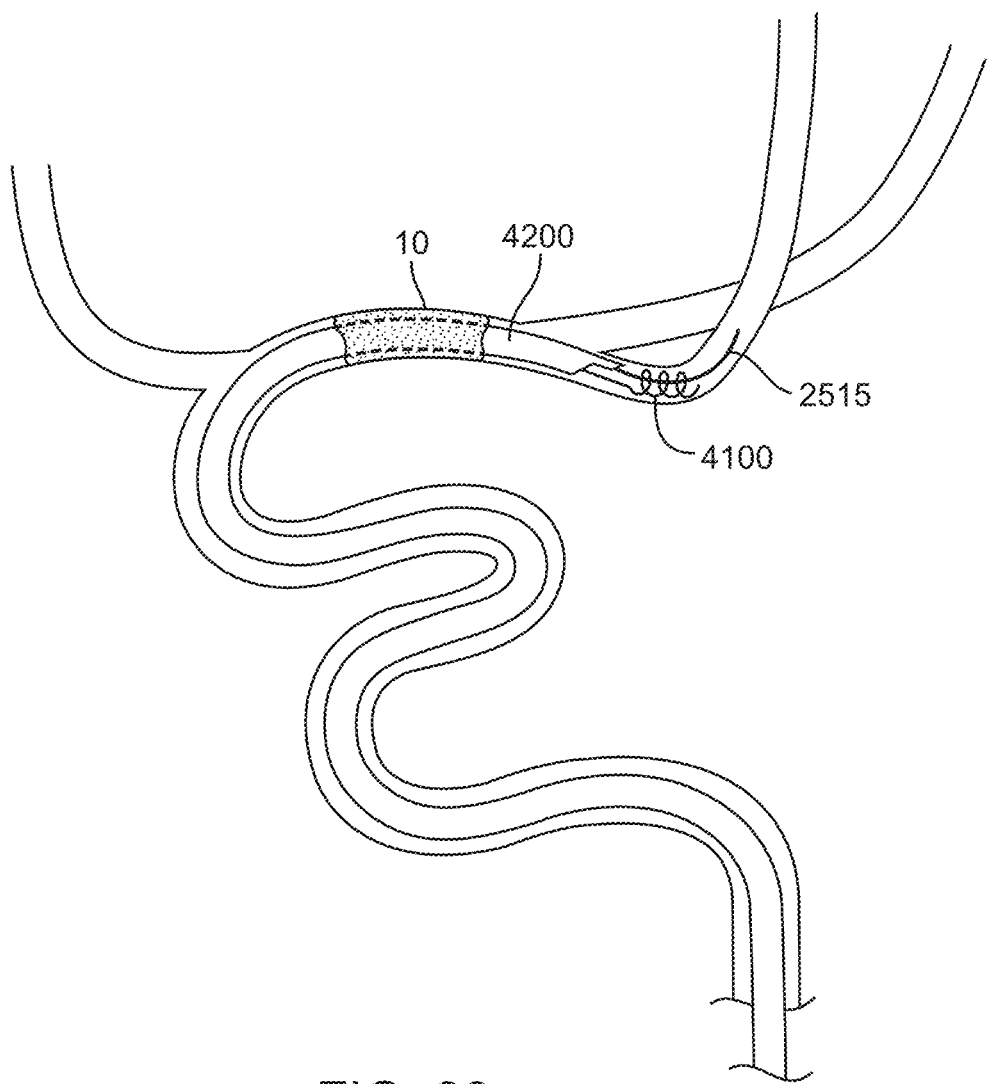
FIG. 30 illustrates an embodiment of a dual-lumen microcatheter.

A major drawback to current thrombectomy devices is the need to re-cross the occlusion with a guidewire and microcatheter if the thrombectomy device did not remove enough of the occlusion to restore adequate flow, and additional attempts are needed to remove the occlusion. Currently, a single-lumen microcatheter is used to deliver the thrombectomy device. The microcatheter is placed over a guidewire, the guidewire is then removed and the thrombectomy device is delivered. When removing the occlusion both the microcatheter and device are pulled back and the access across the occlusion is lost. Thus if the attempt at removal was unsuccessful or incomplete and an additional attempt is required, the guidewire and microcatheter must again cross the occlusion. As mentioned above, this extra step of re-crossing the occlusion takes time and incurs risk of distal vessel injury. An embodiment of this disclosure, shown in FIG. 30, is a microcatheter 4200 which includes at least two lumens, one lumen for a guide wire 2515 and the second to deliver a thrombectomy device 4100 such as a stentriever or coil retriever. The presence of a second lumen for the guide wire may add outer profile to a microcatheter over a microcatheter with just a single lumen. However, the reduced time and risk that may be provided by a second guidewire lumen can be advantageous. In addition, for use transcervically, the guidewire and/or the catheter walls may be scaled down to be less than conventional wall thicknesses, to lower the overall increase needed to add the extra lumen.

Exemplary Embodiments of Perfusion Devices

In an embodiment, the system may include a means to perfuse the cerebral vasculature distal to the thrombotic blockage and ischemic brain tissue via a perfusion catheter delivered, for example, through the arterial access device 2010 to a site distal to the thrombotic occlusion 10. The perfusion catheter is adapted to deliver a perfusion solution to a desired location. Perfusion solution may include, for example, autologous arterial blood, either from the flow line of a passive reverse flow circuit 3500 or from another artery, oxygenated solution, or other neuroprotective agent. In addition, the perfusion solution may be hypothermic to cool the brain tissue, another strategy which has been shown to minimize brain injury during periods of ischemia. The perfusion catheter may also be used to deliver a bolus of an intra-arterial thrombolytic agent pursuant to thrombolytic therapy. Typically, thrombolytic therapy may take up to 1-2 hours or more to clear a blockage after the bolus has been delivered. Mechanical thrombectomy may also take up to 1 to 2 hours to successfully recanalize the blocked artery. Distal perfusion of the ischemic region may minimize the level of brain injury during the stroke treatment procedure. Embodiments of distal perfusion means are described below.

Figure 31:
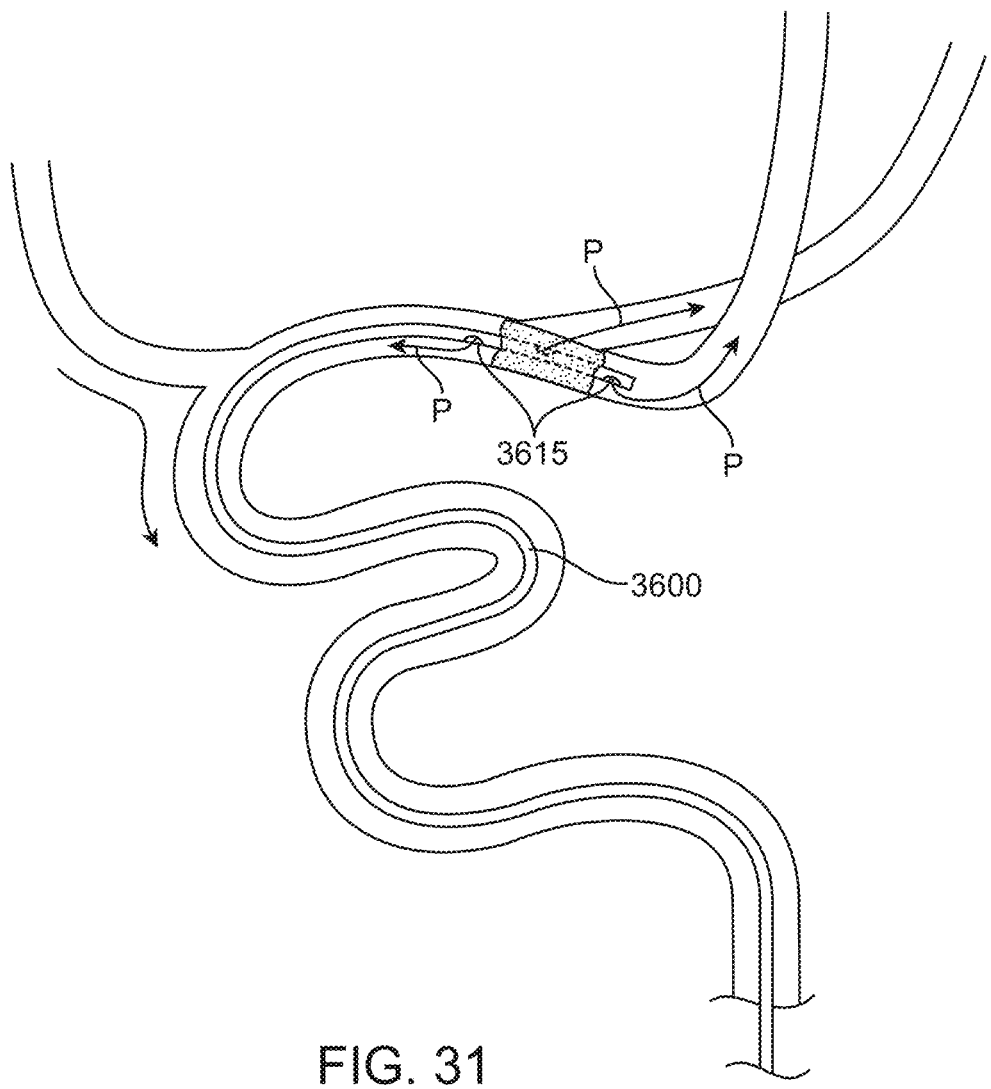
FIG. 31 illustrates an embodiment of a distal perfusion catheter.

FIG. 31 shows a perfusion catheter 3600 positioned across the thrombotic blockage 10, to enable perfusion distal to the blockage. In an embodiment, the catheter is 3600 positioned over a guidewire placed through a lumen in the catheter. The lumen may serve as both a guidewire lumen and a perfusion lumen. Once placed, the guidewire may be removed to maximize the throughspace of the lumen available for perfusion. Alternately, the guidewire lumen and the perfusion lumen may be two separate lumens within the catheter, so that the guidewire may remain in place in the guidewire lumen during perfusion without interfering with the perfusion lumen. Perfusion exit holes 3615, which communicate with the perfusion lumen, are located in a distal region of the catheter 3600. This perfusion lumen may be connected to a perfusion source such as a perfusion pump or syringe and may be used for perfusing fluid such as neuroprotective agents and/or oxygenated blood such as the patient's own arterial blood via the perfusion exit holes 3615 as exhibited by the arrows P in FIG. 32, which represent the flow of perfusion solution out of the catheter 3600. Alternately, the catheter 3600 may be positioned relative to the blockage 10 such that the perfusion exit holes 3615 are initially positioned just proximal to, or within, the thrombotic blockage 10 during a bolus of thrombolytic infusion. The catheter can then be re-positioned so that at least some of the perfusion exit holes 3615 are located distal of the blockage 10 to provide distal perfusion with blood or an equivalent solution to the ischemic penumbra. The perfusion catheter may be used in conjunction with mechanical or aspiration thrombectomy as above. The catheter may be positioned through the lumen of access device 2010 or distal catheter 2030. The catheter may be placed side by side with mechanical thrombectomy means in the lumen, or may be co-axial with mechanical thrombectomy device.

FIG. 32 shows another embodiment of a perfusion catheter 3600 with a perfusion lumen 3610 that communicates with side holes 3615 and/or an end opening 3616 for perfusing fluid, and a second lumen 3612 for pressure monitoring. The pressure monitoring lumen 3612 is closed off at a distal-most end 3613. A side opening 3614 to the lumen 3612 is located proximal of the distal-most end 3613 for measuring perfusion pressure. The catheter 3600 is shown without an expandable occlusion element although it could include an expandable occlusion element such as an occlusion balloon. The occlusion element may be positioned either distal to or proximal to the side holes 3615. In an embodiment, the perfusion source may be controlled by the perfusion pressure measurement to maintain perfusion pressure below 200 mm Hg. In an embodiment, the perfusion flow rate is controlled to maintain perfusion in the range of about 50 ml/min to about 250 ml/min.

Figure 33:
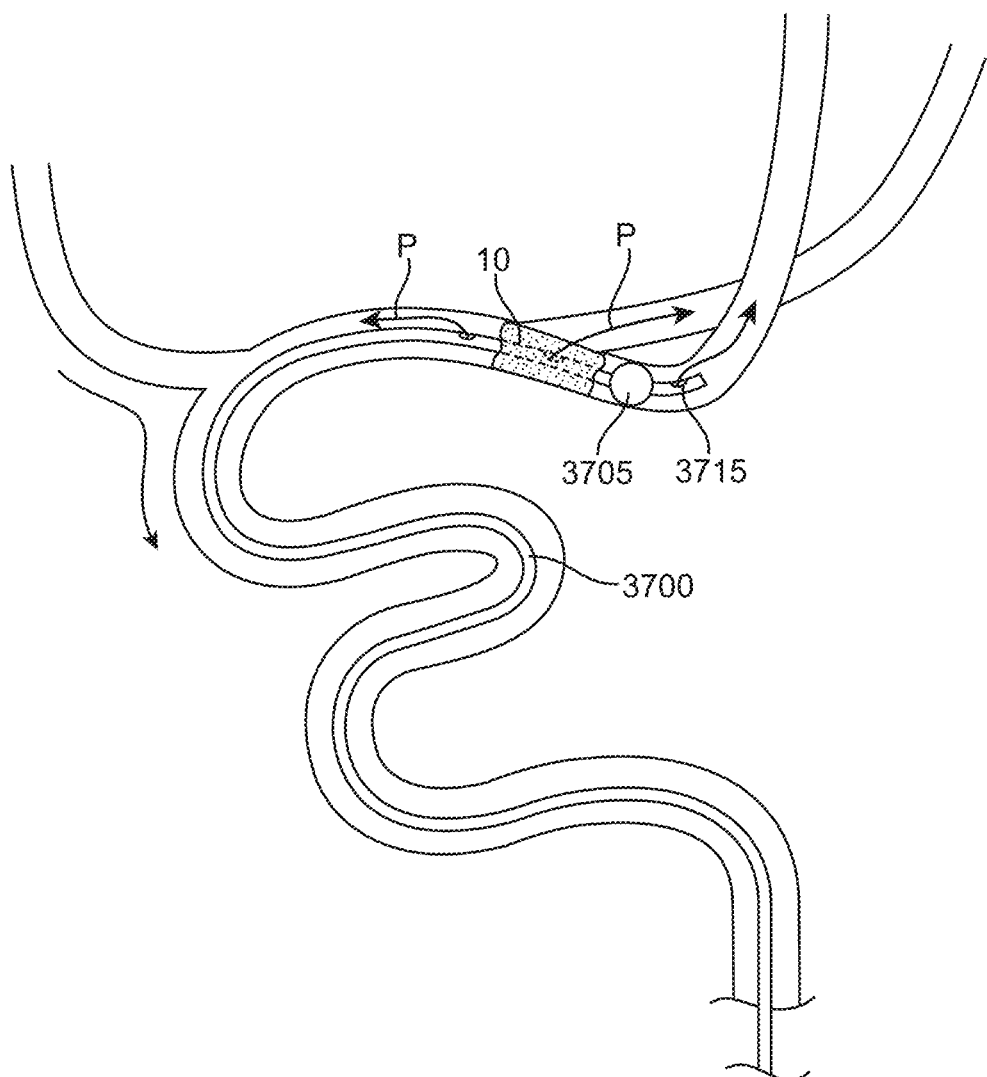
FIGS. 33-36 illustrate different embodiments of distal perfusion catheters with an occlusion balloon.
Figure 34:
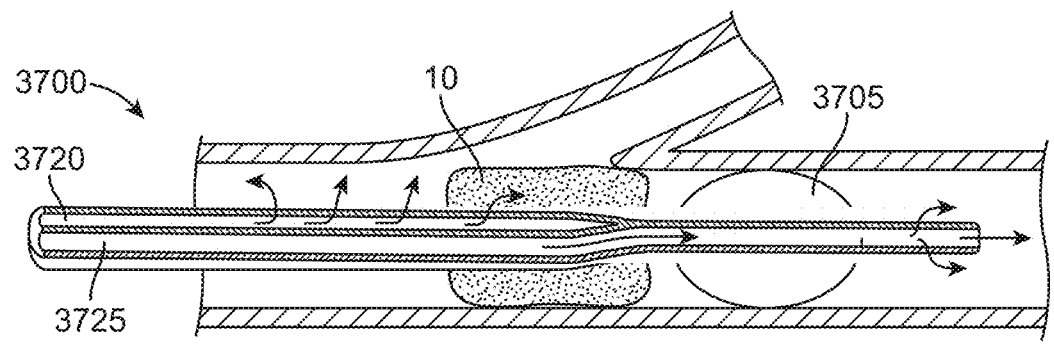
Figure 35:
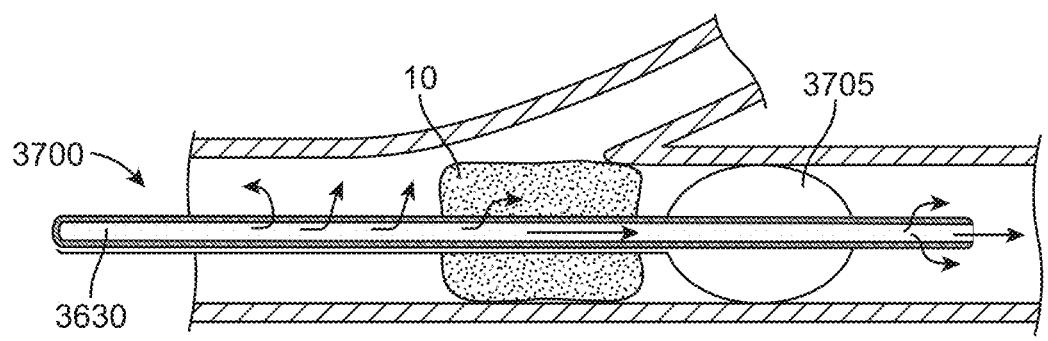

In an alternate embodiment, as shown in FIG. 33, distal perfusion catheter 3700 includes an occlusion balloon 3705, with perfusion exit holes 3715 positioned distal to, and/or proximal to the occlusion balloon 3705. As with the previous embodiment, the perfusion catheter 3700 may be used in conjunction with recanalization therapies such as thrombectomy devices, aspiration means or intra-arterial thrombolytic infusion. The catheter 3700 is placed in the vasculature so that the occlusion balloon 3705 is positioned distal to the blockage 10. The catheter 3700 may be configured to perfuse the region distal of the balloon 3705 with blood or equivalent, and the region proximal of the balloon 3705 with thrombolytic agents. In this regard, the catheter 3700 may include separate perfusion lumens 3720 and 3725 that communicate with separate perfusion exit holes, as shown in FIG. 34. Alternately, as shown in FIG. 35, the distal and proximal perfusion exit holes are connected to the same perfusion lumen 3630, and regions both distal and proximal to the occlusion balloon are used to infuse blood or alternate perfusion solution. Not shown in either FIG. 34 or 35 is a separate lumen for inflation and deflation of occlusion balloon 3705. This lumen may be embedded into the wall of the catheter.

Figure 36:
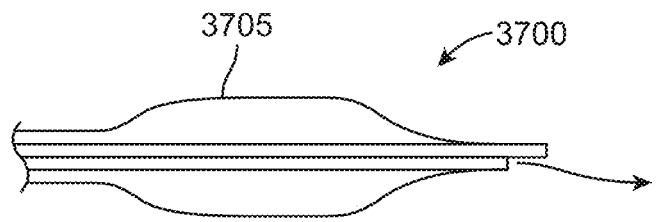

In another embodiment, as shown in FIG. 36, the expandable occlusion device 3705 is a dilatation balloon which may provide a dilatation force on the thrombus while the catheter 3700 is perfusing the distal vasculature.

Figure 37:
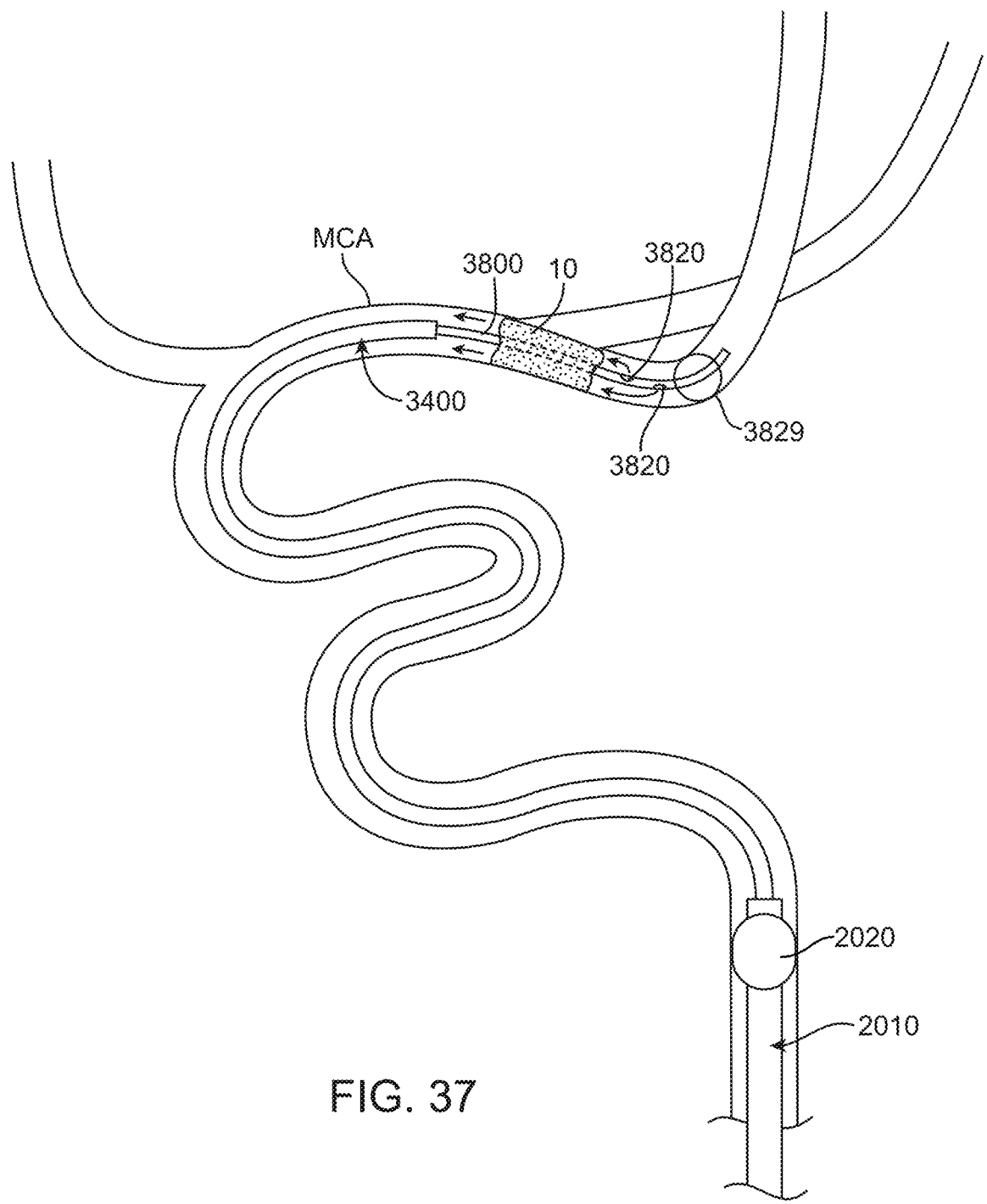
FIG. 37 illustrates another embodiment of a distal perfusion catheter.

The perfusion catheter may also provide perfusion to aid in thrombus removal. FIG. 37 shows a proximal perfusion catheter 3800 being deployed distal of the occlusion via the arterial access device 2010. The proximal perfusion catheter 3800 includes an expandable occlusion element 3829 such as an occlusion balloon. The proximal perfusion catheter 3800 also includes one or more perfusion exit holes 3820 at a location proximal to the occlusion element 3829. The perfusion exit holes 3820 communicate with an internal perfusion lumen in the perfusion catheter 3800 for perfusion of fluid out through the perfusion exit holes 3820. With reference still to FIG. 37, the proximal perfusion catheter 3800 is deployed into the vasculature via the arterial access device so that the occlusion element 3829 of the perfusion catheter is positioned and expanded distal to the thrombus 10 with the perfusion exit holes 3820 positioned proximal to the occlusion element 3829 and distal to the thrombus 10. Such an arrangement provides back pressure to assist in removal of the thrombus 10. In addition, the occlusion element 3829 serves as distal emboli protection. Any of a variety of perfusion fluids may be used including, for example, oxygenated blood, neuroprotection agents, thrombolytics, as well as other fluids, which may be adjusted to a desired temperature. The arterial access device 2010 can be used for aspiration in the arrangement of FIG. 37. The arterial access device 2010 may have occlusion balloon 2020 as well as passive or active aspiration means. The perfusion catheter facilitates removal of the thrombus into the arterial access device 2010 and thence through the flow line 2025 and out of the patient.

Figure 38:
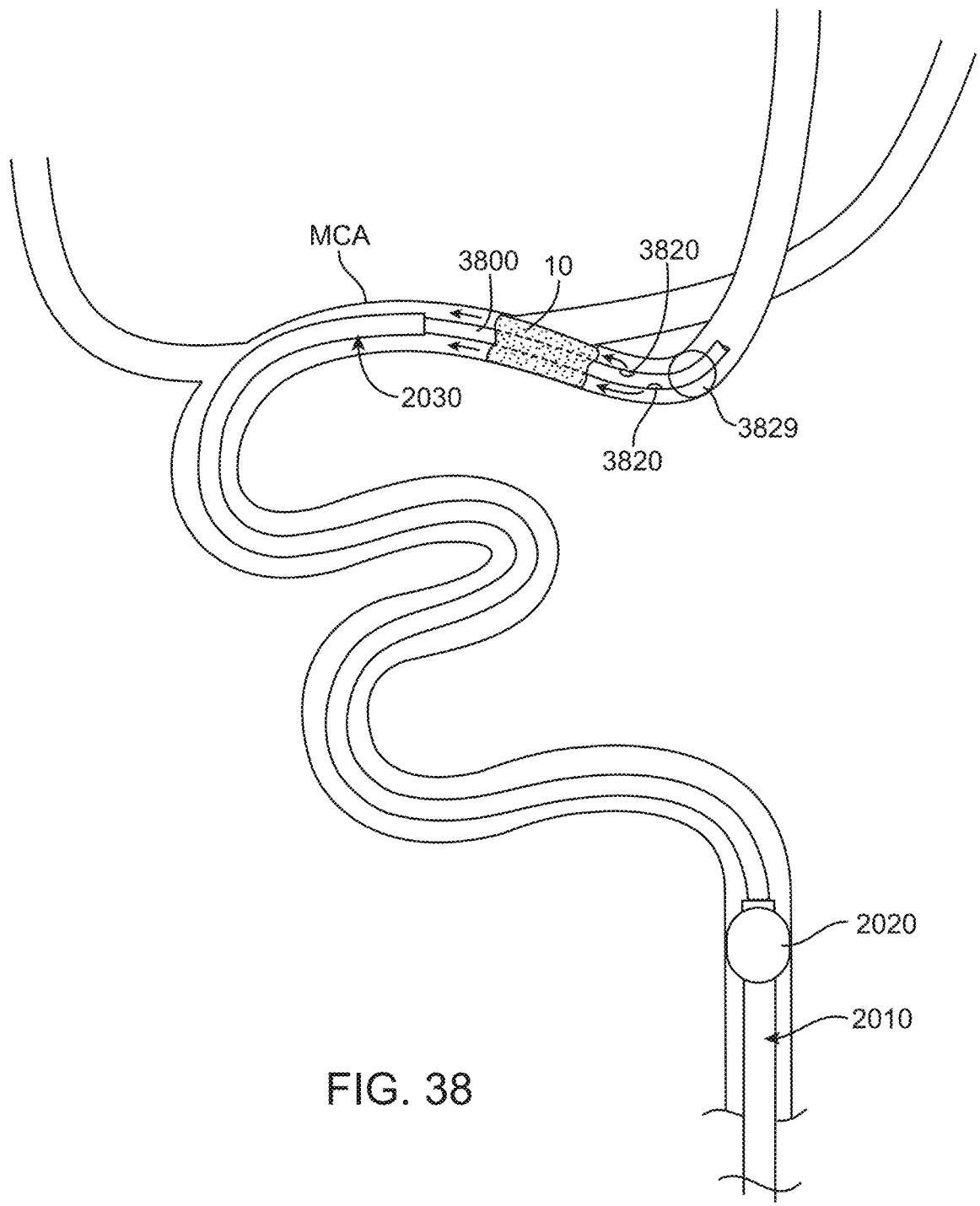
FIG. 38 illustrates an embodiment of the system with the addition of a distal balloon catheter configured to perfuse proximal to the balloon.

Alternately, as shown in FIG. 38, the proximal perfusion catheter 3800 may be delivered via distal catheter 2030. When aspiration is initiated through the distal catheter 2030 and perfusion is initiated through proximal perfusion catheter 3800 there is a pressure gradient in a retrograde direction which aids in removal of thrombus 10 from the vessel, and into the lumen of distal catheter 2030. The arterial access device 2010 and distal catheter 2030 may simultaneously aspirate. Or, the aspiration may be applied sequentially between the arterial access device 2010 and the distal catheter 2030. For example, the distal catheter 2030, when positioned as shown in FIG. 38, can aspirate. The distal catheter 2030 can then be withdrawn into the arterial access device 2010 and the aspiration applied from the arterial access device.

In addition to providing pressure distal to the occlusion, the perfusion fluid from proximal perfusion catheter 3800 can supply blood to smaller vessels (perforators) originating in or just proximal to the occlusion. The shaft of the perfusion catheter 3800 may also be used as a rail or conduit for delivery of a therapeutic device such as stentriever or thrombectomy device.

In an embodiment, the perfusion lumen and the guide wire lumen are two separate lumens, configured for example as in FIG. 32. In an alternate embodiment, the perfusion lumen of the perfusion catheter 3800 also serves as a guide wire lumen. In such an arrangement, a valve is desirably located at the distal end opening of the perfusion/guide wire lumen. When the guide wire is pushed distally out of the distal end opening of the guide wire lumen, the guide wire opens the valve. The valve automatically closes when the guide wire is retracted proximally back into the lumen. In this manner, the valve seals the distal end opening of the lumen after the guide wire is retracted. The valve can also be a pressure relief valve such that if the perfusion pressure is too high, the valve opens to release the pressure.

Figure 39A:
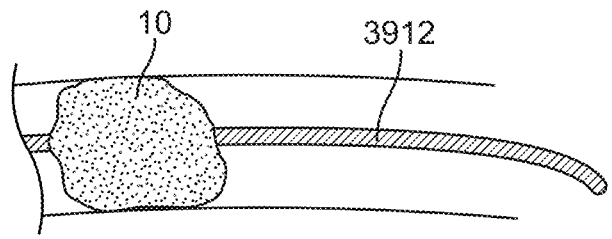
FIGS. 39A-39D illustrates steps in usage of a distal balloon catheter configured to perfuse distal and/or proximal to the balloon.
Figure 39B:
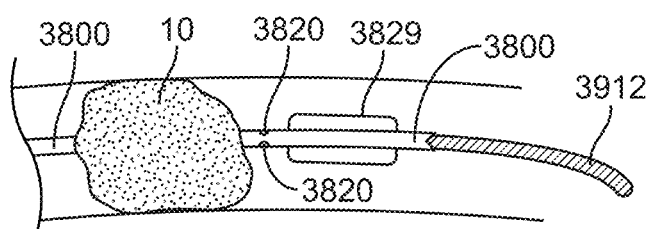
Figure 39C:
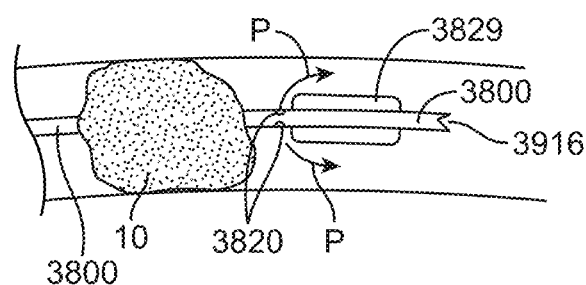
Figure 39D:
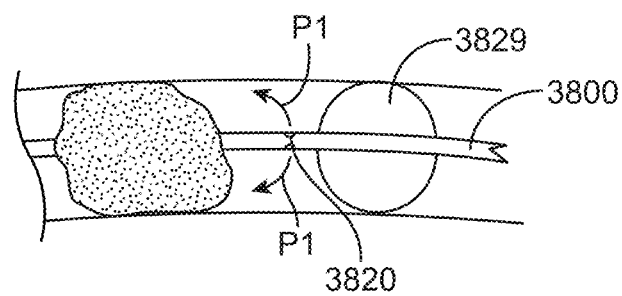

FIGS. 39A-39D show an exemplary method of use of proximal perfusion catheter 3800. FIG. 39A shows an enlarged view of a guide wire 3912 positioned across the thrombus 10 in a cerebral artery. In FIG. 39B, a distal region of the perfusion catheter 3800 has been positioned across the thrombus 10 (via the guide wire 3912) with the unexpanded occlusion element 3829 positioned distal of the thrombus 10. The guide wire 3912 protrudes out of the distal end of the guide wire lumen of the perfusion catheter 3800. In FIG. 39C, the guide wire is not shown as it has been retracted back into the guide wire lumen of the perfusion catheter 3800. If the guide wire lumen also serves as a perfusion lumen for the perfusion catheter 3800, a distal valve 3916 (such as a duckbill valve) at the distal end of the guide wire/perfusion lumen has automatically closed such that the lumen can now be used for perfusion via the perfusion exit holes 3820, as represented by the arrows P in FIG. 34C. When the occlusion element 3829 is unexpanded (as shown in FIG. 39C), the perfusion exit holes 3820 can be used to perfuse distally. In FIG. 39D, the expandable occlusion element 3829 has been expanded in the artery. The perfusion exit holes 3820 can then be used for perfusion proximal of the occlusion element 3829, as represented by the arrows P1 in FIG. 39D.

Perfusion catheters 3600 or 3800 may include an element for monitoring blood pressure. In an embodiment, the pressure monitoring element is a dedicated internal lumen in the perfusion catheter 3600 or 3800, wherein the lumen is fluid-filled and connected to a pressure transducer on the proximal end of the perfusion catheter. A pressure transducer on the catheter itself may also be used. Alternately, a pressure measuring guide wire may be inserted through an internal lumen of the perfusion catheter 3600 or 3800 to a location where pressure is to be monitored.

An alternate means for cerebral perfusion comprises cerebral retroperfusion as described by Frazee et al. This embodiment involves selective cannulation and occlusion of the transverse sinuses via the internal jugular vein, and infusion of blood via the superior sagittal sinus to the brain tissue, during treatment of ischemic stroke. The following articles, which are incorporated herein by reference in their entirety, described cerebral retroperfusion and are incorporated by reference in their entirety: Frazee, J. G. and X. Luo (1999). "Retrograde transvenous perfusion." Crit Care Clin 15(4): 777-88, vii.; and Frazee, J. G., X. Luo, et al. (1998). "Retrograde transvenous neuroperfusion: a back door treatment for stroke." Stroke 29(9): 1912-6. This perfusion, in addition to providing protection to the cerebral tissue, may also cause a retrograde flow gradient in the cerebral arteries. Used in conjunction with the system 100, a retroperfusion component may provide oxygen to brain tissue, as well as aid in capture of embolic debris into the reverse flow line during recanalization of the thrombotic occlusion 10.

It should be appreciated that other perfusion catheters or systems may be used with the system 100, for example those described by U.S. Pat. Nos. 6,435,189 and 6,295,990, which are incorporated by reference in their entirety.

Exemplary Methods and Devices for Transcervical Vessel Closure

Any type of closing element, including a self-closing element, a suture-based closing element, or a hydrostatic seal element, may be deployed on or about the penetration in the wall of the common carotid artery prior to withdrawing the arterial access device 2010 or introducer sheath 2110 (the procedural sheath) at the end of the procedure. The following U.S. patent applications, which are incorporated herein by reference in their entirety, describe exemplary closure devices and methods: U.S. Patent Publication No. 20100042118, entitled "Suture Delivery Device", and U.S. Patent Publication No. 20100228269, entitled "Vessel Closure Clip Device".

The closing element may be deployed at or near the beginning of the procedure in a step termed "pre-closure", or, the closing element could be deployed as the sheath is being withdrawn. In an embodiment, the means for vessel closure is a suture-based blood vessel closure device. The suture-based vessel closure device can place one or more sutures across a vessel access site such that, when the suture ends are tied off after sheath removal, the stitch or stitches provide hemostasis to the access site. The sutures can be applied either prior to insertion of the procedural sheath through the arteriotomy or after removal of the sheath from the arteriotomy. The device can maintain temporary hemostasis of the arteriotomy after placement of sutures but before and during placement of a procedural sheath, if a pre-closure step us used, and can also maintain temporary hemostasis after withdrawal of the procedural sheath but before tying off the suture. Some exemplary suture-based blood vessel disclosure devices are described in the following U.S. patents, which are incorporated herein by reference in their entirety: U.S. Pat. Nos. 6,562,052; 7,001,400; and 7,004,952.

In an embodiment, the system includes an ultrasound probe element, which when used with an ultrasound imaging system is configured to identify the desired site of carotid arterial access to determine that is suitable for percutaneous puncture, for example to verify that there is no vascular disease in the vessel. The probe will also visualize surrounding anatomy such as the internal jugular vein, to ensure that access can be achieved without comprising these other structures. In addition, the probe may be used to visualize the access site after vessel closure to verify that hemostasis has been achieved. If needed, the probe may be used to provide localized compression at the site of the puncture as needed to ensure hemostasis. For example, after vessel closure the probe is used to image the closure site. If blood is seen flowing from the site, the probe is pressed down to compress the site. The user periodically relaxes the pressure on the probe to assess if hemostasis has been achieved. If it has not, pressure is reapplied. If it has, the probe may be removed.

Exemplary Methods of Use

As illustrated in FIG. 1, the arterial access device 2010 is transcervically introduced directly into the common carotid artery CCA of the patient. This may be done with a percutaneous puncture or a direct cut-down. In the case of a puncture, ultrasound imaging may be used to accurately make the initial arterial puncture. The arterial access device 2010 is threaded through the vasculature such that the distal tip is positioned in the common carotid artery or the proximal or distal cervical, petrous, or cavernous portion of the internal carotid artery ICA. A removable proximal extension may be used to place the arterial access device 2010 under fluoroscopy without exposing the user's hand to radiation. U.S. patent application Ser. No. 12/834,869, filed Jul. 12, 2010, describes exemplary embodiments of removable proximal extensions and is incorporated herein by reference.

Once the arterial access device is positioned, a diagnostic angiogram may be performed via a microcatheter placed through the arterial access device. The microcatheter may be for angiographic injections both proximal and distal to the occlusion. Diagnostic angiograms are performed throughout the procedure to determine the progress in removing the occlusion or occlusions.

If the arterial aspiration device has an occlusion balloon, the balloon may be inflated at this time and aspiration may be applied to the arterial access device. Because the tip of the aspiration device is some distance proximal to the occlusion, the aspiration force is not directly applied to the occlusion. However, in some cases, this proximal aspiration may service to remove some or all of the occlusion. Once aspiration from the access device is finished, the occlusion balloon may be deflated so that antegrade flow may resume in the artery.

A distal catheter 2030 is placed through the arterial access device and positioned such that the distal tip reaches the site of the occlusion. If desired, a coaxial system of devices comprising a guide wire, a microcatheter, and the distal catheter 2030 are inserted together through the arterial access device 2010 and advanced towards the cerebral occlusion. Alternately, a tapered dilator with or without a microcatheter tip may be substituted for the microcatheter. Alternately, a microcatheter and guide wire may be placed inside the tapered dilator. The removable proximal extension, if used, may be removed prior to introduction of the telescoping devices, or the devices may be inserted through the removable proximal extension. The microcatheter, or tapered dilator, and guide wire are then advanced to access and cross the cerebral occlusion. The microcatheter or dilator may be used to perform the angiogram of the cerebral circulation proximal and distal to the occlusion. The microcatheter may also be used as a rail to advance the distal catheter.

Typically, the largest size distal catheter will be selected which is able to be safely navigated to the occlusion, to maximize the force and luminal area for aspiration of the occlusion. Aspiration is then initiated through the distal catheter, This may be done manually, with an aspiration pump or other aspiration source, or via the flow controller as described above. If the thrombus is too large or too strongly embedded into the vasculature such that it is not possible to remove the occlusion via aspiration alone, further steps are taken to remove the occlusion. A thrombectomy device may be deployed through the arterial access device to remove the clot. During clot retrieval, passive or active aspiration may be applied via the arterial access device to minimize or eliminate the amount of distal emboli.

If the distal catheter is unable to reach the occlusion, or if a secondary more distal occlusion needs to be reached after removal of a first occlusion, a second, smaller diameter distal catheter may be inserted through the first distal catheter, and positioned at the site of the occlusion. Alternately, the first distal catheter may be removed and exchanged for the second distal catheter. A guidewire and/or microcatheter may be placed through the first distal catheter to facilitate the exchange. Once at the target site, aspiration may be initiated through the second catheter as above, or additional devices may be inserted to aid in removal of the occlusion.

If there is difficulty navigating the distal catheter of the desired size to a location just proximal to the clot, a device may be deployed distal to the clot and expanded to act as an anchor to aid in advancing the distal catheter as shown in FIG. 6 or 7. If desirable, a second distal catheter may be used in a telescoping manner to create support for the first distal catheter to access the proximal face of the occlusion. Alternately, a tapered dilator as shown in FIG. 8 may be used in addition to or in place of the microcatheter to facilitate navigation of the distal catheter. The arterial access device 2010 and the distal catheter 2030 may be connected to means for passive or active aspiration, as shown in FIGS. 15-17, or a flow controller 3400 as shown in FIG. 18. In one embodiment, the arterial access device 2010 is connected to passive aspiration and the distal catheter 2030 is connected to active aspiration. In another embodiment, both devices are connected to active aspiration. During the procedure, the user may open or close the connections to the passive and/or active aspiration sources as desired. For example, when the distal catheter 2030 is positioned at the proximal face of the clot, the active aspiration may be initiated to apply suction to the occlusion with the goal to remove the occlusion. If a locking syringe was used and an additional aspiration step is desired, the syringe may be removed, emptied, reattached and re-locked for additional aspiration.

In another embodiment, the microcatheter is used to deliver a thrombectomy device such as a coil or stentriever in or beyond the occlusion. The device is then pulled towards the distal catheter to remove the occlusion, aided by aspiration of the distal catheter. The occlusion is then pulled back using the distal catheter, thrombectomy device, and/or microcatheter into the arterial access device. In yet another embodiment, the microcatheter has two lumens as shown in FIGS. 11 and 12, such that the guide wire may be left across the occlusion when the microcatheter and/or thrombectomy device are pulled proximally to remove the occlusion.

At any time during the procedure, the balloon on the arterial access device may be inflated at this point to reduce forward arterial pressure on the occlusion. The inflated balloon may also increase the stability of the arterial access in the vessel to increase the support for advancement of devices through the arterial access device. Additionally, the arterial access device may be connected to passive or active aspiration as desired to provide embolic protection while not compromising collateral flow to the ischemic penumbra of the patient. This may be accomplished by selective periods of reverse, stopped, and antegrade flow, for example reverse flow initiated during periods when the occlusion is being pulled towards and/or entering the guide catheter. Multiple devices or sizes of devices may be used as needed to remove the occlusion or occlusions. At the conclusion of the procedure, the arterial access catheter may be exchanged for a shorter introducer sheath and a vessel closure device may be used to achieve hemostasis at the access site. Ultrasound may again be employed, in this instance to ascertain and/or ensure hemostasis. If appropriate, the ultrasound probe may be used to apply pressure at the access site until hemostasis is achieved.

In a variation of this procedure, the arterial access device is inserted through an introducer sheath which has been previously inserted into the CCA. An example of this configuration is shown in FIG. 2. In this scenario, the arterial access device may be removed and cleared onto a table during the procedure in case the device becomes blocked and aspiration is slowed or stopped, or may be exchanged for another size or type of catheter as needed without loss of arterial access. In addition, there is no need to exchange the sheath at the conclusion of the procedure before utilizing a vessel closure device. The introducer sheath may incorporate a removable proximal extension such that during the procedure there is limited exposure of radiation to the users' hands. If used, the proximal extension may be removed prior to closure of the access site with a vessel closure device.

In yet another embodiment, the system may be used to deliver intra-arterial thrombolytic therapy, such as through a sidearm in the arterial access device 2010. For example, thrombolytic therapy may be infused to the thrombotic occlusion 10 through the arterial access device 2010, or through the distal catheter 2030. In another embodiment, the system may be used to deliver intra-arterial thrombolytic therapy via a micro catheter which is inserted into the arterial access device 2010. The micro catheter is delivered to the site of the thrombotic occlusion 10 to infuse a thrombolytic drug. The thrombolytic therapy may be delivered either in conjunction with or as an alternative to mechanical thrombectomy or aspiration.

In yet a further embodiment, the system is used to provide distal protection and/or perfusion during the procedure. In this embodiment, a perfusion catheter is inserted through the arterial access device 2010 or through the distal catheter 2030, and positioned across the lumen and inflated at a point distal to the occlusion. The perfusion catheter may be connected to a perfusion pump to perfuse oxygenated blood or perfusion solution to the ischemic brain via a distal opening in the perfusion catheter. In an embodiment, the perfusion catheter is a balloon-tipped catheter. The balloon is inflated at a point distal to the occlusion. This balloon acts to prevent emboli from progressing distally during removal or recanalization of the occlusion. The perfusion catheter may also be connected to a flush source to perfuse proximal to the occlusion balloon via proximal ports in the perfusion catheter. This maneuver essentially provides a back pressure on the occlusion and may aid it its removal.

In the instance where there is also a carotid artery stenosis which requires treatment either before or after treatment of the cerebral occlusion, an angioplasty balloon or stent may be deployed in the stenosis via the introducer sheath. If embolic protection is desirable during intervention of the carotid stenosis, the introducer sheath may have an occlusion balloon and a connection to a reverse flow line as shown in FIG. 3, and the CAS procedure may be conducted under reverse flow embolic protection as described in co-pending U.S. patent application Ser. No. 12/176,250, which is incorporated herein by reference. The introducer sheath is then used to place the arterial access device into the ICA. Alternately, the introducer sheath may have two occlusion balloons as shown in FIG. 4, with an opening to allow balloon angioplasty or stenting of the carotid stenosis, and subsequent introduction of devices such as a distal catheter into the ICA and cerebral circulation for treatment of the cerebral occlusion.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A system for intracranial access through a patient's vasculature to access an intracranial occlusion, the system comprising:
   an inner member for steering and advancing through the patient's vasculature, the inner member having a distal tip region, a tapered section and a proximal section, wherein an axis of the inner member passes centrally through the proximal section, the tapered section, and at least partially through the distal tip region, wherein the proximal section, proximal to the distal tip region, has a cylindrical surface having an outer diameter greater than the distal tip region, wherein the proximal section is configured to advance the inner member through the vasculature, and wherein the proximal section, the tapered section, and the distal tip region have a passage therethrough configured for passage and relative movement of a wire; and
   a distal access catheter operatively connected to the inner member and wherein the distal access catheter has a distal inner diameter substantially corresponding to the outer diameter of the cylindrical surface, wherein the cylindrical surface of the inner member is maintained at least partially distal of a distal end of the catheter during advancement through the patient's vasculature, and wherein the inner diameter of the distal access catheter and the outer diameter of the cylindrical surface are sized to prevent coaxial separation between the inner member and the distal edge of the distal access catheter while being advanced through the curved vasculature and the cylindrical surface has a length to allow torsional and coaxial movements of the inner member relative to the distal access catheter while being advanced through curved vasculature without causing separation of the inner member from the distal inner diameter of the distal access catheter.

2. The system of claim 1, wherein the inner member is composed of a flexible material.

3. The system of claim 1, wherein the distal tip region and the tapered section are integral with each other.

4. The system of claim 1, wherein the inner member can move coaxially relative to the distal access catheter.

5. The system of claim 1, wherein the passage has a diameter between about 0.020 inches and 0.024 inches.

6. The system of claim 1, wherein the passage has a diameter between about 0.030 inches and 0.040 inches.

7. The system of claim 1, wherein the passage has a diameter between about 0.042 inches and 0.044 inches.

8. The system of claim 1, further comprising a stent retriever disposed in the passage of the distal tip region.

9. The system of claim 1, further comprising a radiopaque marker disposed at a distal end of the distal tip region.

10. The system of claim 9, wherein the radiopaque marker is fabricated from a material selected from the group consisting of: platinum/iridium, tungsten, platinum, and tantalum-impregnated polymer.

11. The system of claim 1, wherein the inner member is constructed with variable stiffness, wherein a distal segment of the inner member is constructed of a softer material with successively stiffer materials towards a proximal end of the inner member.

12. A method of accessing an intracranial occlusion through a patient's vasculature, the method comprising:
   advancing an inner member through the patient's vasculature, the inner member having a distal tip region, a tapered section, and a proximal section, the inner member having an axis passing centrally through the proximal section, the tapered section, and at least partially through the distal tip region, wherein the proximal section, proximal to the distal tapering surface has a cylindrical surface having an outer diameter greater than a diameter of the distal tip region, wherein the proximal section is configured to advance the inner member through the vasculature, wherein the proximal section, the tapered section, and the distal tip region have a passage therethrough configured for passage and relative movement of a wire, and wherein the inner member is operatively connected to a distal access catheter having a distal inner diameter substantially corresponding to the outer diameter of the cylindrical surface and wherein the distal access catheter can move coaxially relative to the cylindrical surface;
   maintaining the distal tapering surface partially outside of a distal end of the distal access catheter while being advanced through a curved portion of the patient's vasculature and while causing torsional and coaxial movements of the inner member relative to the distal access catheter, the distal inner diameter of the distal access catheter and the outer diameter of the cylindrical surface being sized and having a length to prevent separation between the inner member and a distal edge of the distal access catheter; and
   manipulating the inner member and distal access catheter through the patient's vasculature by a combination of torsional movements of the inner member and coaxial movements of the inner member relative to the distal access catheter to move the distal access catheter through regions of the patient's vasculature having a high tortuosity and without causing coaxial separation of the cylindrical surface from the distal inner diameter of the distal access catheter.

* * * * *